US005726298A

United States Patent [19]

Hirai et al.

[11] Patent Number: 5,726,298
[45] Date of Patent: Mar. 10, 1998

[54] EPIMORPHIN AND ITS ENCODING NUCLEIC ACIDS

[75] Inventors: Yohei Hirai, Chigasaki; Makoto Takashina; Kyoko Takebe, both of Yokohama, all of Japan

[73] Assignee: Biomedical Research Institute Co., Ltd., Kanagawa, Japan

[21] Appl. No.: 690,457

[22] Filed: Aug. 16, 1996

Related U.S. Application Data

[63] Continuation of Ser. No. 78,309, filed as PCT/JP92/01340, Oct. 15, 1992 published as WO93/08213, Apr. 29, 1993, abandoned.

[30] Foreign Application Priority Data

| Oct. 16, 1991 | [JP] | Japan | 3-294856 |
| Oct. 16, 1991 | [JP] | Japan | 3-294857 |
| Apr. 17, 1992 | [JP] | Japan | 4-122906 |
| Apr. 30, 1992 | [JP] | Japan | 4-135692 |

[51] Int. Cl.$^6$ .......................... C12N 15/12; C07K 14/435
[52] U.S. Cl. .......................... 536/23.5; 530/350; 435/69.1; 435/69.7
[58] Field of Search .......................... 530/350; 536/23.5; 435/69.1, 69.7

[56] References Cited

PUBLICATIONS

*Development Growth & Differentiation;* Published by The Japanese Society of Developmental Biologists; ISSN 0012-1592; vol. 32, No. 4, pp. 424, 807, Aug. 1990.
Montesano et al., Cell, vol. 69, 697–711, 1991.
Jahoda et al., Nature, vol. 311, 560–562, 1984.
Hirai et al., Cell, vol. 69, p. 471, 1992.
Inoue et al., Biochemical and Biophysical Res. Commun. vol. 187, p. 1144, 1992.
John M. Chirgwin et al "Isolation of Bioligocally Active Ribonucleic Acid From Sources Enriched in Ribonuclease", Biochemistry No. 18, pp. 5294–5299, American Chemical Society, 1979.
T. V. Rhynh et al, DNA Cloning, "Constructing and Screening cDNA Libraries in gt10 and gt11", IRL Press 1984, pp. 48–78.

*Primary Examiner*—Sally P. Teng
*Attorney, Agent, or Firm*—Cushman Darby & Cushman IP Group of Pillsbury Madison & Sutro, LLP

[57] ABSTRACT

Novel physiologically active substance designated as epimorphin which is capable of being expressed by a gene hybridizing with a gene probe composed of the base sequence complementary to part of the base sequence of Sequence ID No. 1 in Sequence Listing, and which is produced by mesenchymal cells derived from human or mouse, and which shows morphogenetic activity of epithelial tissue, and isoforms of said epimorphin, base sequences encoding them, modified epimorphin, in which hydrophobic region at the carboxy terminal of said epimorphin polypeptide has been deleted or replaced by non-hydrophobic polypeptide, and polyclonal antibody or monoclonal antibody produced by the use of a full length or a part of said epimorphin as an antigen are provided. The substances of the present invention can be used for elucidation of the mechanism of diseases caused by abnormal epithelium formation, diagnosis of said diseases, or development of therapeutic methods therefor.

14 Claims, 8 Drawing Sheets

FIG. 1
  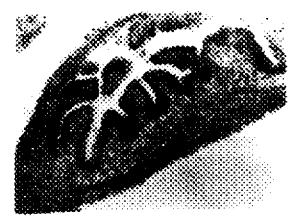
Control
  
In the Presence of mAb12
Skin          Lung          Small Intestine

| 3T3 | 3T3 to which Epimorphin cDNA was introduced |
|---|---|
| ↓ | ↓ |

— ← Epimorphin

FIG. 5
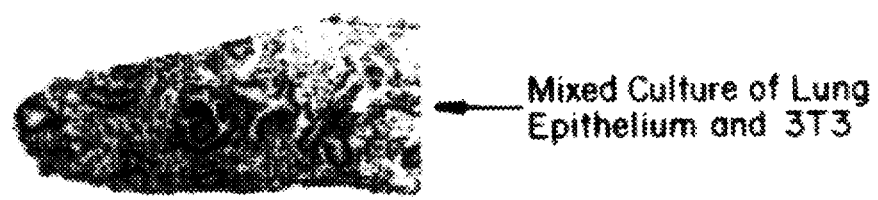
Mixed Culture of Lung Epithelium and 3T3
Mixed Culture of Lung Epithelium and Epimorphin Transfectant

FIG. 9
10th Day after Initiation of Culture
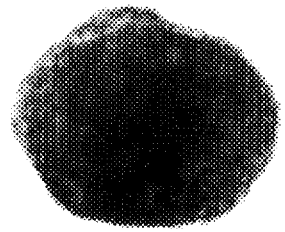
↑
3T3 + Lung Epithelium
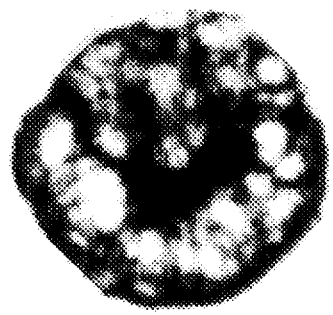
↑
Epimorphin Expression
Transfectant
+
Lung Epithelium
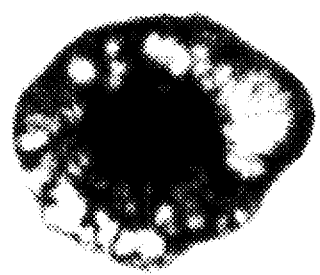
↑
Soluble Epimorphin Expression
Transfectant Lacking C-terminal
Hydrophobic Region
+
Lung Epithelium

FIG. 10
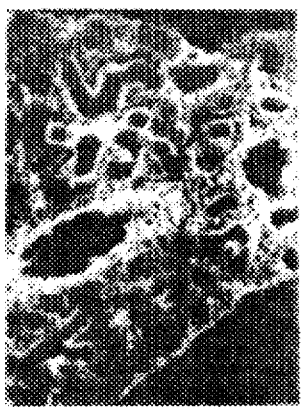
Fetal Lung
at 15th Day
Fetal Skin
(Folliculus pili)
at 16th Day
Fetal Small
Intestine at
15th Day

EPIMORPHIN AND ITS ENCODING NUCLEIC ACIDS

This is a continuation of application Ser. No. 08/078,309, filed on Jun. 15, 1993, now abandoned, which is a 371 application of international application PCT/JP92/01340, filed Oct. 15, 1992 published as WO93/08213, Apr. 29, 1993.

The present invention relates to a physiologically active substance designated as "epimorphin" by the present inventors, which exists broadly in mesenchymal tissues such as skin, lung, intestine or the like, of mammals including mouse and human, and which is essential to morphogenesis of epithelial tissue. More particularly, this invention relates to said physiologically active substance, epimorphin, its variants, genes encoding epimorphin, and polyclonal antibodies or monoclonal antibodies to epimorphin. Thus, the present invention provides a powerful means for elucidating the mechanism of onset of diseases caused by disorder during epithelialization, for developing diagnostic and therapeutic methods of such diseases, and finding novel methods for curing wounds.

Since normal organization and morphogenesis of the epithelium undergo some control of mesenchyme and since most of the diseases caused by disorder of the epithelial forms are due to the mesenchyme existing around them, a lot of studies have long been made on the mechanism through which the mesenchyme supports the morphogenesis of epithelium. However, any significant development has not been accomplished in the isolation, purification and structure analysis of the molecule which controls the morphogenesis of epithelium, since the subject matter of the studies is a substance which is expressed under temporal and spatial control in a complex system, which makes it difficult to carry out an experiment in a simplified culture system.

In order to elucidate the mechanism of onset of the diseases caused by disorder of the epithelial form and realize the development of a therapy of such diseases, it is an essential premise to isolate and purify the physiologically active substance having an activity of controlling said epithelial forms, which is produced by mesenchymal cells, and elucidate its structure. Thus, it has been an important issue in this field to attain the isolation and purification of said molecule and elucidate its structure.

SUMMARY OF THE INVENTION

For solving such a problem, the present inventors have established an in vitro experimental culture system, which effects the same morphogenesis as in vivo, using skin tissues of an experimental animal, mouse fetus, which tissues show a vigorous morphogenesis. One of the features of this technique consists in separating the cells isolated from a living body into epithelial cells and mesenchymal cells and culturing the mesenchymal cells in a clumping form, although, prior to the present invention, the mesenchymal cells were subjected to monolayer culture to examine their product.

By using this culture system, the present inventors have found that a normal morphogenesis takes place even in vitro only when the epithelium separated from mouse fetus skin contacts with the mesenchymal cells in the clumping form.

For examining a substance which supports the morphogenesis of epithelium and which is produced by the mesenchymal cells in the clumping form, the present inventors immunized a rat with mesenchymal cells cultured in the clumping form as an immunogen to rise rat monoclonal antibodies to the mouse mesenchymal cell and selected an antibody capable of inhibiting the epithelial morphogenesis by binding to the mouse mesenchyme. Then, the resultant antibody was used to investigate the novel substance that binds to this antibody, said substance existing in the mesenchymal tissue and supporting the epithelial morphogenesis. The present inventors have found a novel physiologically active substance (epimorphin) which supports the epithelial morphogenesis, isolated it and succeeded in elucidating its structure, namely its gene sequence and amino acid sequence for the first time. Further, the present inventors have succeeded in identifying other two isoforms of the mouse epimorphin and corresponding human epimorphin and its two isoforms, using the resultant gene.

The genes obtained above were integrated into appropriate expression vectors, which, when introduced into animal cells or *E. coli* cells, allowed the artificial production of epimorphin. This has been clarified by the following experiment.

These products have proved to have an activity of effecting a normal morphogenesis of epithelium when said products are added to an experimental culture system containing the epithelium and the mesenchymal cells which lack the ability to produce epimorphin. In detail, from the fact that, though no normal morphogenesis of epithelium was attained when coculture was effected on a combination of a fetus epithelial tissue and a mesenchymal cell line, which revealed to have nearly lost its capability of producing epimorphin, according to the analysis carried out on its product, a normal morphogenesis of epithelium takes place when an epimorphin gene is transfected into this mesenchymal cell line in order to compel the cell to express epimorphin or by adding epimorphin into the culture medium, the present inventors have confirmed that the products have an activity to effect the morphogenesis of epithelium as mentioned above.

Further, the present inventors have found that there are two kinds of epimorphin, namely epimorphin bound to a cell membrane and secretory type. The epimorphin bound to a cell membrane has a hydrophobic amino acid sequence at the carboxy terminal of the polypeptide and includes mouse epimorphin, Isoform A, one of two sorts of its isoforms, human epimorphin and Isoform A thereof, one of two sorts of its isoforms. The inventors have succeeded in preparing, from said cell membrane binding epimorphin, modified epimorphin of a soluble type which is secreted from cultured animal cells into the culture medium, and which can be purified and isolated more easily than natural epimorphin, by deleting a polypeptide fragment up to about one fifth from the carboxy terminal, said terminal polypeptide containing the hydrophobic protein moiety with which the epimorphin binds to the cell membrane, or by replacing the terminal fragment with non-hydrophobic polypeptide. These modified epimorphins comprise an amino acid sequence common to three sorts of epimorphins including isoforms and have been found to show high solubility and effect a similar and normal morphogenesis of the epithelium as the natural epimorphins.

Moreover, the present inventors have succeeded in preparing polyclonal antibodies and monoclonal antibodies capable of binding preferentially to the epimorphin by immunizing an animal such as rabbit, rat, mouse or the like, which is different from the animal species from which the epimorphin has been derived, with epimorphin or its fragment obtained by the above-mentioned method.

On the basis of the above findings, the present inventors have established a method for identification of epimorphin which is novel and essential for morphogenesis of the epithelium and of genes encoding said epimorphin, production, by means of recombinant techhnology, of said epimorphin and modified epimorphin having the same function as epimorphin and having high solubility, production of polyclonal antibodies and monoclonal antibodies useful for examining the expression of said substances and for purifying them. Thus, the present invention provides powerful means for elucidation of the onset of diseases caused by disorders during epithelialization, for developing diagnostic and therapeutic methods of said diseases, or for developing new methods for curing wounds.

Accordingly, an object of the present invention is to provide novel physiologically active substance, epimorphin, existing in mesenchyme of various organs such as skin, lung, intestine or the like of mammals including at least mouse and human, which may be expressed by a gene capable of hybridizing with a gene probe composed of a base sequence complementary to the base sequence depicted in Sequence ID No. 1 in Sequence Listing.

Another object of the invention is to provide said novel physiologically active substance, epimorphin, which has the amino acid sequence of SEQ ID NO. 2 in Sequence Listing, at an amino terminal.

A further object of this invention is to provide novel physiologically active substances, human epimorphin and isoforms of said human epimorphin, which are produced by mesenchymal cells derived from human and essential for morphogenesis of an epithelium, and which are represented by the amino acid sequence of SEQ ID NO: 3, 4 and 5 in Sequence Listing.

Specifically, Sequence ID No. 3 in Sequence Listing shows the amino acid sequence of human epimorphin, Sequence ID No. 4 in Sequence Listing shows the amino acid sequence of another human epimorphin (Isoform A), and SEQ ID NO: 5 shows the amino acid sequence of another human epimorphin (Isoform B), respectively.

A further object of the present invention is to provide genes represented by the base sequences of SEQ ID NO: 6, 7 and 8 in Sequence Listing, which encode said human epimorphin and isoforms of said human epimorphin.

Specifically, SEQ ID NO: 6 in Sequence Listing shows the base sequence of the gene encoding human epimorphin, SEQ ID NO: 7 in Sequence Listing shows the base sequence of the gene encoding another human epimorphin (Isoform A), and SEQ ID NO: 8 in Sequence Listing Shows the base sequence of the gene encoding another human epimorphin (Isoform B), respectively.

Another object of the present invention is to provide a novel physiologically active substances, mouse epimorphin and isoforms of said mouse epimorphin, which are produced by mesenchymal cells derived from mouse and essential for the morphogenesis of an epithelium, and which are represented by SEQ ID NO: 9, 10 and 11 in Sequence Listing.

Specifically, Sequence ID No. 9 in Sequence Listing shows the amino acid sequence of mouse epimorphin, SEQ ID NO: 10 in Sequence Listing shows amino acid sequence of another mouse epimorphin (Isoform A), and SEQ ID NO: 11 in Sequence Listing shows the amino acid sequence of another mouse epimorphin (Isoform B), respectively.

A further object of the present invention is to provide genes represented by the base sequences of SEQ ID NO: 12, 13 and 14, which encode said mouse epimorphin and isoforms of said mouse epimorphin.

Specifically, SEQ ID NO: 12 in Sequence Listing shows the base sequence of a gene encoding mouse epimorphin, SEQ ID NO: 13 in Sequence Listing shows the base sequence of a gene encoding another mouse epimorphin (Isoform A), and SEQ ID NO: 14 in Sequence Listing shows the base sequence of a gene encoding another mouse epimorphin (Isoform B), respectively.

An additional object of the present invention is to provide a soluble modified epimorphin which is obtained by deleting partial amino acid sequence of epimorphin which, at the carboxy terminal, contains hydrophobic amino acid sequence or by replacing the partial sequence with non-hydrophobic polypeptide.

Furthermore, an object of the present invention is to provide a soluble modified human epimorphin and its isoforms which are obtained by deleting partial amino acid sequence at the carboxy terminal of human epimorphin or its isoform which contains hydrophobic amino acid sequence, or replacing the partial sequence with non-hydrophobic polypeptide.

Moreover, an object of the present invention is to provide a soluble modified mouse epimorphin and its isoforms which are obtained by deleting partial amino acid sequence at the carboxy terminal of mouse epimorphin or its isoform which contains hydrophobic amino acid sequence, or by replacing the partial sequence with non-hydrophobic polypeptide.

Further, another object of the present invention is to provide polyclonal antibodies to epimorphin obtained by immunizing a certain animal species different from animal species from which the epimorphin has been derived with said epimorphin or its fragment and collecting the immunized animal serum.

Furthermore, an object of the present invention is to provide monoclonal antibodies against said epimorphin.

Moreover, an object of the present invention is to provide monoclonal antibodies to epimorphin obtained by immunizing a certain animal species different from animal species from which the epimorphin has been derived, with said epimorphin or its fragment and fusing the antibody-producing cell collected from that animal with myeloma cell.

Further, an object of the present invention is to provide monoclonal antibodies to epimorphin obtained by immunizing a rat with mouse epimorphin and fusing the antibody-producing cell collected from the rat with myeloma cell.

Furthermore, an object of the present invention is to provide a process for purifying above-mentioned epimorphins and their isoforms by the use of monoclonal antibody to said epimorphins by taking advantage of antigen-antibody reaction.

Moreover, an object of the present invention is to provide a method of detecting each of the above-mentioned epimorphins and their isoforms by applying antigen-antibody reaction with the use of polyclonal antibody or monoclonal antibody to said epimorphin.

Further, an object of the present invention is to provide said physiologically active novel substance, epimorphin, essential for the morphogenesis of epithelium, its isoforms (Isoform A and Isoform B), a modified epimorphin and its isoforms, polyclonal antibodies and monoclonal antibodies strongly binding to said epimorphin and modified epimorphin or their isoforms, which are all useful for elucidation of onset of diseases caused by disorder during epithelialization, development of diagnostic or therapeutic method of the diseases, or development of novel method for curing wounds.

BRIEF EXPLANATION OF THE DRAWINGS

FIG. 1 shows abnormal epithelial morphogenesis caused by inhibition of epimorphin activity by the antibody of the present invention.

FIG. 5 shows the tissue slices which indicate an ability of supporting the form of pulmonary epithelium under culture with NIH/3T3 into which epimorphin cDNA has been introduced or not introduced.

FIG. 9 shows the results of the culture experiment which exhibited that both epimorphin containing the hydrophobic region at the C-terminal and epimorphin without hydrophobic region at the C-terminal have an ability of morphogenesis of the pulmonary epithelium.

FIG. 10 shows the result of examination of expression pattern of epimorphin using the antibody of the present invention, wherein brightly stained portion indicates abundance of expressed epimorphin.

DETAILED EXPLANATION OF THE INVENTION

Figure 2:
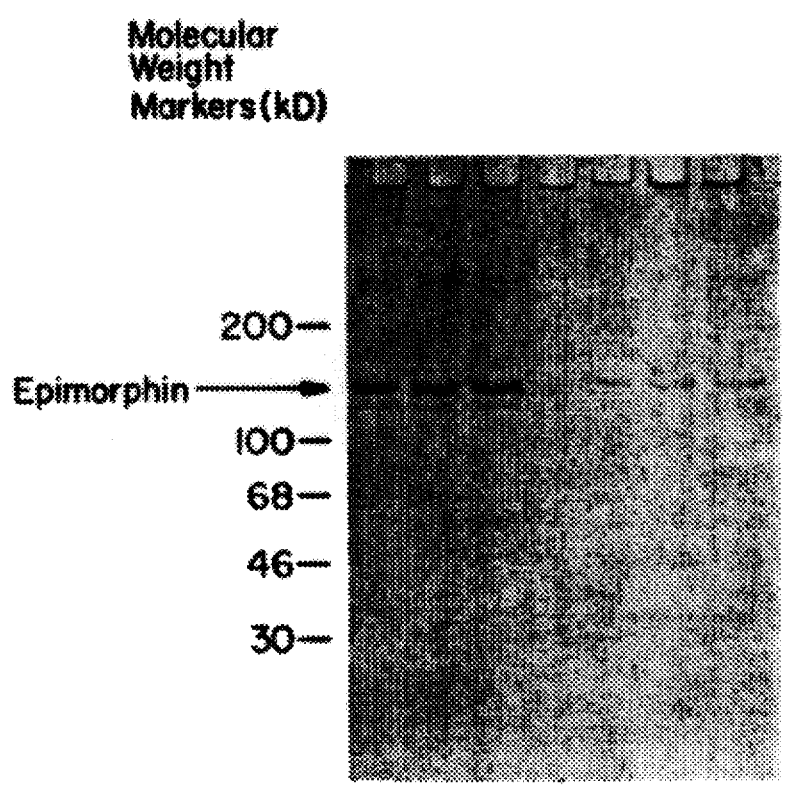
FIG. 2 shows an electrophoresis pattern of epimorphin purified by the use of the antibody of the present invention.

The epimorphin of the present invention is a substance which is biosynthesized by the mesenchymal cell and which comprises a protein consisting of 277 to 289 amino acid residues as a core protein. It is modified in an animal cell so as to have a molecular weight of about 150 K dalton in mouse and about 70 K dalton in human (sodium dodecyl sulfate polyacrylamide gel electrophoresis). There exist at least three types of epimorphin due to gene splicing. One type (epimorphin Isoform B) is a secretion type, and other two types (epimorphin and epimorphin Isoform A) have a binding property to cell membrane because they have the hydrophobic sequence consisting of 20 to 30 amino acid residues at the carboxy terminal. These molecules exist in the mesenchyme and exert an important function in controlling the epithelial morphogenesis. This was confirmed from the fact that no normal morphogenesis of the epithelium was observed when epimorphin didn't function well in an experiment wherein an antibody which inhibits the function of epimorphin was added to organ cultures of skin, intestine, or lung, or in an experiment wherein a combination of an epithelial tissue and mesenchymal cells having the lowered ability of producing epimorphin was cultured. Further, this was confirmed from the fact that in the latter experiment, the normal morphogenesis of the epithelium was recovered by adding epimorphin to the culture.

When the distribution or existence of epimorphin was examined by staining a tissue with an antibody, namely when a tissue slice is reacted with an antibody against epimorphin for coloring, it was found that epimorphin exists intensively at the border line between the mesenchyme and the epithelium under morphogenesis, or its neighbourhood in mesenchyme, or within the mesenchyme close to the region in which the epithelial fission was prosperous, in particular, at the time of fetal genesis or anagenesis.

For example, epimorphin is intensively expressed at the border region between dermis and epidermis and in the mesenchyme near the top of immature hair follicle, which is considered to induce the follicular development, at the time of fetal genesis or anagenesis in the skin tissue. Further, epimorphin is intensively expressed in the mesenchyme contacting the epithelium in which luminal genesis and branching are taking place, in small intestines or lungs at the time of fetal genesis.

As stated above, epimorphin is intensively expressed at the time of histogenesis within the mesenchyme close to the epithelium, in which histogenesis is taking place, but epimorphin is produced only in the mesenchymal cell and not in the epithelial cell.

About 90% homology is found in the amino acid sequence between mouse epimorphin and human epimorphin. Thus, it was found that the homologous sequence was preserved well among different animal species.

Furthermore, a group of epimorphin molecules found by the present inventors commonly possess the amino acid sequence represented by SEQ ID NO: 2 in Sequence Listing at the amino terminal, and this amino acid sequence at the amino terminal was found to be different from that of known proteins originating in living bodies.

Since the amino acid sequence at the amino terminal common to this group of epimorphin molecules is based on the gene having the same or almost the same base sequence represented by SEQ ID NO: 1 in Sequence Listing, it has been found that every gene encoding one of the epimorphin molecules can be detected and identified by using a complementary strand to the base sequence represented by SEQ ID NO: 1 in Sequence Listing as a probe.

The epimorphin of the present invention can be obtained from various animal mesenchymal cells. However, the epimorphin of the present invention should be construed to include those which are obtained by the modification of said natural epimorphin through deletion, insertion, or addition of part of amino acids, without damaging the epimorphin activity.

The gene of the invention which encodes the epimorphin of the present invention also includes those which are obtained by replacing one or more bases of the natural gene with other base or bases so that the replacement retains the property of producing the same amino acid and those which are obtained by deleting, inserting or adding one or more bases from or to the natural gene without causing damage to the activity of epimorphin encoded by these genes.

In this text, only the base sequence of a single strand is disclosed, and the complementary base sequence is omitted.

The epimorphin of the present invention and a DNA fragment of the gene encoding the same can be obtained, for example, by the following methods.

(Preparation of mRNA)

A connective tissue of the organ such as skin, small intestine, lung, placenta, or navel string, or an established cell line originating from the mesenchyme is homogenized in an aqueous solution of guanidium thiocyanate, and all RNAs are separated as a precipitate by cesium chloride density-gradient centrifugation according to Chirgwin et al. [Biochemistry, 18, 5294–5299 (1979)] or by sucrose density-gradient centrifugation. After separation, all RNAs are purified by extraction with phenol and precipitation with ethanol, and the RNAs are chromatographed on a column of oligo (dT) cellulose to isolate a pool of poly (A) mRNAs containing the objective mRNA encoding epimorphin. The pool of mRNAs is further purified by sucrose density-gradient centrifugation to enrich a content of the objective mRNA encoding epimorphin for the purpose of increasing the possibility of attaining the desired gene.

(Cloning of a gene encoding epimorphin)

As described in detail below, cDNA library is prepared, using the above-noted mRNAs as a starting material, according to, for example, the method using λ phage vector as described by Huynh et al. [DNA Cloning, 49–78, IRL Press (1984)]. On the other hand, an antibody is prepared by immunizing an animal (e.g. rat) different from the animal from which the above-noted mRNAs have been obtained, with mesenchymal cells of the latter animal (e.g. mouse). This antibody must be anti-epimorphin monoclonal antibody which has been confirmed to react with epimorphin mainly based on its inhibitory action on epimorphin activity. A gene encoding epimorphin is identified and separated using this antibody according to Young et al. [Proc. Natl. Acad. Sci. USA, 80, 1194 (1983)] by examining whether or not a translation product of cDNA is bound to the antibody.

The procedure of cloning will be described below.

(First Step)

The pool of mRNAs prepared above is hybridized with a primer cDNA such as oligo (dT) primer, and double stranded cDNA is prepared, for example, according to Gubler et al. method [Gene, 25, 263 (1983)] by using reverse transcriptase and cDNA polymerase I.

Gubler et al. method consists of the following steps: a single stranded cDNA complementary to the mRNA is prepared using reverse transcriptase; *E. coli* RNase H and DNA polymerase I are successively added thereto to give double stranded cDNA containing cDNA in place of mRNA; and T4 DNA polymerase is added thereto in order to smooth both ends of the double stranded cDNA.

(Second Step)

An adaptor having an enzyme cleavage site such as EcoRI site at one end is added to both ends of the cDNA chain obtained above.

(Third Step)

A pool of recombinant λ phage DNAs or recombinant plasmid DNAs is prepared by inserting the cDNA chain into enzyme cleavage site such as EcoRI site of λ phage vector (e.g. λgt11) or plasmid vector having a promoter capable of translating the cDNA chain.

(Fourth Step)

λ Phage granules containing recombinant λ phage DNA may be obtained by so-called in vitro packaging. Thus, by using commercially available in vitro packaging kit such as Giga Pack II Gold (Stratagene Company) or the like, and following the attached protocol, the λ phage granules are obtained by the use of the pool of λ phage DNAs obtained above as raw material. That is, a lysate of *E. coli* containing mutant phage lysogen is used as a protein source necessary for phage granular formation to prepare in vitro λ phage containing the recombinant X DNA in granule [Hohn et al., Proc. Natl. Acad. Sci. USA, 74, 3259 (1977)]. The resultant λ phage granule is allowed to incorporate into a host such as *E. coli* or the like by infection and allowed to grow therein.

Where the recombinant plasmid DNAs are used, a host like *E. coli* is transformed with them in conventional manner and allowed to grow.

(Fifth Step)

The clone producing a part of epimorphin is identified by using the anti-epimorphin antibody in the following manner. By using an appropriate reagent, such as isopropyl β-thiogalactopyranoside (IPTG) where a vector having lac promoter is used, bacteria are allowed to produce proteins including the introduced DNA product. Next, the proteins are allowed to absorb on a membrane like nitrocellulose and the membrane is allowed to react with anti-epimorphin antibody and then with a secondary antibody labelled with radio-active material in that order.

Once a part of cDNA encoding epimorphin has been obtained, the cDNA in full length containing non-coding region of epimorphin and even cDNA encoding epimorphin of other animal species can be easily isolated, for example, by the following method, using the partial cDNA as a probe.

Thus, the same procedures as the procedures described above beginning from "Preparation of mRNA" and ending at "Fourth Step" are effected using a connective tissue of animal species to be identified and the following alternative fifth step is effected as a next step.

(Alternative Fifth Step)

A clone, in which the full length or part of epimorphin gene: has been integrated, is identified by transferring the above-noted DNAs to an appropriate membrane having a nucleic acid binding ability, such as nylon membrane, denaturing the DNAs with an alkali or the like, and hybridizing with a probe of epimorphin gene which has previously been obtained and labelled, for example, with a radioactive material.

Polymerase chain reaction (PCR) method [Methods Enzymol., 155, 335–350 (1987)] is an alternative method for isolating cDNA which encodes epimorphin of other animal species, and employs the epimorphin-encoding cDNA obtained above. Thus, since epimorphin gene has high homology between animal species, it is possible to obtain cDNA encoding isoforms of epimorphin or epimorphin of other animal species as a gene of high homology by selecting, as a starting site for amplification of unidentified epimorphin gene, a region having low homology with other materials in the cDNA base sequence, including the non-coding region, of epimorphin, adding the region to cDNAs prepared and purified from the mesenchymal cells, and amplifying the complementary chain using polymerase.

(Expression of cDNA)

Expression of cDNA thus obtained can be effected, for example, by using a transient in vitro protein translation system, specifically, the translation system using oocyte of *Xenopus laevis* as described in Nature, 329, 836–838 (1987) or by using a translation system within a host cell such as *E. coli* or established animal cell line into which there has been introduced a plasmid conventionally employed for expression of protein, which is obtained by connecting in phase said DNA with the initiation codon ATG locating downstream to a promoter of a plasmid such as pUC 19 or the like. Then, the epimorphin of the present invention can be obtained, for example, by recovering the protein expressed by the use of an affinity column conjugated with anti-epimorphin antibody.

(Preparation of modified epimorphin)

The soluble and easily operable modified epimorphin having the same function as the natural epimorphin can be prepared by cutting epimorphin molecule itself in a biochemical process. However, it is preferable to obtain the modified epimorphin by modifying a gene encoding natural epimorphin and producing the modified epimorphin using such modified gene. Though there is no limitation to the method for the modification, the sequence encoding hydrophobic region can be cut and deleted using a restriction enzyme, or a frame shift can be induced upstream to the sequence so as to avoid correct translation of the continuous hydrophobic amino acids. Where the hydrophobic amino acid sequence is to be replaced by non-hydrophobic amino acid sequence, the gene encoding the hydrophobic amino acid sequence is deleted and a gene encoding the desirous non-hydrophobic amino acid sequence is inserted into the deleted region, which gives the gene encoding the desired modified epimorphin. Thus, the part encoding hydrophobic region at C terminal of epimorphin can be deleted or replaced by the gene encoding non-hydrophobic amino acid sequence by incorporating cDNA which has been isolated by various methods as mentioned above into an animal cell expression vector and the like and subjecting it to a conventional procedure such as digestion by the use of an appropriate restriction enzyme such as HincII, and smoothing at the terminus, and relinking.

The modified epimorphin can be prepared by introducing the modified epimorphin gene into an appropriate vector (e.g. pBluescript II, pUC19, CDMS, etc.) and transfecting it into $E.\ coli$ cell or an animal cell, followed by culturing the host cell under appropriate conditions for expressing the introduced gene. In the case of the former, the modified epimorphin polypeptide is recovered from the supernatant of the lysate of the microorganism. In the case of the latter, the modified epimorphin is recovered from the culture supernatant. Said recoveries are attained by various methods, for example, by applying appropriate immunoaffinity chromatography.

The soluble modified epimorphin or modified epimorphin polypeptide thus obtained has a property of being easily soluble in physiological solution. Accordingly, they can be easily produced or purified in a large scale and advantageously used in various ways. For example, they are usable as it is for elucidation of abnormal epithelial morphogenesis and for diagnosis and therapy thereof.

Production and purification steps of epimorphin or modified epimorphin obtained by various methods as mentioned above are very enormous and complicated, and give poor yield of epimorphin, and there remains a big problem in providing materials for actual research and development and also applied development. Further, as for measurement of epimorphin, it is necessary to consider inferiority in operability and accuracy in the measurement when the amount is determined as an activity based on the morphological change of epithelial tissue by means of bioassay, and it is also necessary to consider the presence of contaminants which interfere with the assayed data. These problems can be solved by using polyclonal or monoclonal antibody which specifically binds to the epimorphin, and which is obtainable by the use of the epimorphin obtained by the above-noted procedure. Thus, immunologically purifying means of epimorphin and immunologically measuring means of epimorphin can be provided by applying the polyclonal antibody or monoclonal antibody of the present invention. The polyclonal antibody and monoclonal antibody of the present invention is characterized in that they have a specific binding ability to epimorphin, and such antibodies include those inhibiting or not inhibiting the activity of epimorphin. Further, anti-epimorphin antiserum is included in the polyclonal antibody of the present invention.

The polyclonal antibody and monoclonal antibody to epimorphin can be prepared by using a full length epimorphin or its fragment obtained by various methods as mentioned above as immunogen, according to conventional productions of antibodies. There is no need to use purified epimorphin, and crude products such as cells and tissues containing epimorphin can be used in the production of the antibodies of the present invention.

The polyclonal antibodies of the present invention can be prepared by immunizing mammals such as rats, mice, hamsters, rabbits, goats, or the like with said immunogen and repeating the same immunization until a group of antibodies, present in partially collected serum, binding hard to the immunogen are detected. The type of animal species used for immunization is not limited, as far as the animal species different from animal species from which the immunogen originates is used. Immunization is effected in a conventional manner, for example, by administering said immunogen to mammal by intravenous, subcutaneous or intraperitoneal route. More specifically, the immunization is preferably effected by administering several times, every 2 to 21 days, a solution or suspension of immunogen appropriately diluted with phosphate buffer saline (PBS) or the like, and if necessary, together with a conventional adjuvant which activates the immunoreaction so that the total amount of the immunogen may be about 100 to 500 μg/animal. The antiserum, namely crude polyclonal antibody, can be prepared by collecting blood from the sensitized animal and separating the serum component. The resultant antiserum is purified in a conventional manner, using dialysis, salting out with conc. ammonium sulfate solution, gel filtration, or affinity chromatography to which anti-immunoglobulin antibody has been bound or the like, to give the objective polyclonal antibody. The reactivity of the polyclonal antibody can be raised by the immuno-affinity chromatography using purified immunogen.

The monoclonal antibody of the present invention can be prepared by immunizing a mammal in the manner similar to the above mentioned production of the polyclonal antibody to the epimorphin, fusing an antibody-producing cell collected from the animal with myeloma cell of a mammal so as to produce a group of fused cells (hybridomas), selecting from the group a clone of hybridoma producing an antibody which recognizes the immunogen, and allowing the clone to produce the objective monoclonal antibody. Appropriate animal species suitable for immunization are preferably selected under consideration of adaptability to the myeloma cell used for cell fusion and preferably includes Armenian hamster, mouse, rat and the like. When the epimorphin derived from mice often used in experiments is employed, the monoclonal antibody can be prepared even by using neighboring species such as rat as an animal to be immunized. As an antibody-producing cell, spleen cells extracted about three days after the final immunization with an immunogen are preferably used. The myeloma cell to be used for fusing with said antibody-producing cell includes various known cells such as P3×63Ag8 (ATCC TIB 9), P3×63Ag8. U. 1 (ATCC CRL 1597), P3/NSI/1-Ag4-1 (ATCC TIB 18), Sp2/0-Ag14 (ATCC CRL 1581), FO (ATCC CRL 1646), P3 ×63Ag8. 653 (ATCC CRL 1580), S194/5. XXO. BU. 1 (ATCC TIB 20), etc. or YB2/0 (ATCC CRL 1662) etc. in rat.

Fusion of the antibody-producing cell with myeloma cell can be effected, for example, according to the method of Milstein et al. [Methods Enzymol., 73, 3–46 (1981)]. More specifically, said fusion can be effected, for example, in conventional nutrient medium in the presence of a fusion accelerator. Conventional fusion accelerators illustratively include polyethylene glycol (PEG), Sendai virus (HVJ) and the like, and a supplementary agent like dimethyl sulfoxide can be added for raising the fusion efficiency, if necessary. Ratio of the antibody-producing cell to myeloma cell to be used is conventional and, for example, about 1 to 10 fold of the immunocompetent cells to myeloma cells are used. As a medium used for the fusion, various media such as RPMI-1640 medium, MEM medium and the like, which are used for growing said myeloma cell, are used. However, it is preferred that, in general, serum supplement like fetal bovine serum is previously omitted.

Fusion is effected by mixing a predetermined amount of the antibody-producing cell and myeloma cell in the above-noted medium and adding a solution of PEG previously warmed at 37° C., for example, PEG having an average molecular weight of about 1000 to 6000 at a concentration of about 30 to 60% (w/v) and mixing it with the medium. A hybridoma is produced by repeating the procedures consisting of adding appropriate medium successively, centrifuging and removing the supernatant. Separation of the resultant hybridoma is effected by culturing in a conventional selection medium, for example, HAT medium (a medium containing hypoxanthine, aminopuierin and thymidine). Culture in said HAT medium may be effected for a period of time enough to kill and diminish cells other than hybridoma (those cells not fused yet), in general, for several days to several weeks. The hybridoma thus obtained is subjected to a conventional limiting dilution by which the objective antibody-producing cell is selected and monocloned.

Selection of antibody-producing strain can be effected by various methods, for example, by ELISA (enzyme-linked immunosolvent assay), generally used for detection of an antibody [Hybridoma Method and Monoclonal Antibody, published by K. K. R & D Planning, pp 30–53, Mar. 5, 1982]. Thus, the binding ability to an immunogen possessed by the monoclonal antibody contained in the culture supernatant of cloned hybridoma can be evaluated by adding to the immunogen fixed on a solid phase the culture supernatant of cloned hybridoma and an enzyme-labelled antibody to immunoglobulin of the animal species used for the immunization successively and with the following washing, and finally examining the degree of coloring developed by the addition of a substrate solution inducing the color reaction with the labelled enzyme. Purified immunogen is preferably used as an antigen for the above selection.

The hybridoma thus obtained which produces the desirous monoclonal antibody can be subjected to subculture in a conventional medium such as RPMI-1640 containing serum and can be preserved for a long period of time in liquid nitrogen.

Recovery of the monoclonal antibody of the present invention from said hybridoma can be effected by culturing said hybridoma in a conventional manner and collecting the culture supernatant, or by administering the hybridoma to a mammal having an adaptability thereto so that the hybridoma may grow therein, and collecting the ascites fluid. The former is suitable for obtaining highly pure antibody, and the latter is suitable for mass production of the antibody.

The monoclonal antibody obtained by the above method can be purified in the same manner as in the purification of polyclonal antibody as mentioned above.

Epimorphins including modified epimorphins can be easily and specifically purified using the polyclonal antibody or monoclonal antibody of the present invention thus obtained according to conventional immunological purification procedures such as immuno-precipitation, immuno-affinity chromatography, protein A column and the like. Further, the epimorphins can be easily assayed in high sensitivity, high accuracy and high specificity by conventional immunological means such as radioimmunoassay (RIA), enzymatic immunoassay (EIA), fluorescent antibody method or the like.

EXAMPLE

Although the present invention will be explained concretely by the following examples, the scope of the present invention should not be limited to said examples.

Example 1. Preparation of Monoclonal Antibody Against Mouse Epimorphin a) Dermal cells of fetal mouse having epimorphin on the surface of the cell membrane were used as immunogen. On the basis of findings by the present inventors that, while epimorphin is produced in the mesenchymal cell cultivated in the clumping form, supporting the epithelial morphogenesis, epimorphin is hardly produced in the monolayer mesenchymal cell culture having flat cytomorphology, with which the epithelial morphogenesis does not take place, the mesenchymal (dermal) cells isolated from the skin tissue of five experimental animals, ICR fetal mice, were cultured in the clumping form for 4 days, homogenized and suspended in a physiological saline in the following procedure.

1) The skin tissues of five fetal mice removed from ICR mice (Japan Charles River) on the 13th day of pregnancy were cut off with operating scissors and washed with physiological saline.

2) The skin tissues of fetal mice prepared in 1) were incubated in HEPES-Hanks' solution (pH 7.4) containing 0.25% trypsin and 10 mM $CaCl_2$ at 4° C. for 12 hours, then mixed with 20 μg/ml DNAase and gently pipetted to give sheet-form epidermis and isolated dermal cells.

3) The cell suspension obtained in 2) was centrifuged at a low speed to remove the epidermis from the dermal cells in the supernatant. In the subsequent procedures, a 1:1 mixed medium (DH medium) of Dalbecco's Modified Eagle medium (DME) and Ham F12 medium, containing 10% fetal bovine serum, was used.

4) The isolated dermal cells were washed with the medium, and then centrifuged at 1,000 rpm for 2 minutes. Each 100 μl aliquot was sucked with a micropipette from the resulting pellet of dermal cells, put on a porous NUCLEOPORE™ membrane (diameter 13 mm: pore diameter 8 μm) floating on the medium, and cultured in the clumping form.

5) The above dermal cells cultured at 37° C. for 4 days under 5% $CO_2$ conditions were suspended in a serum-free medium, washed, and then dispersed in physiological saline for using as antigen.

To this suspension, an equal amount of Freund complete adjuvant (Difco Laboratories, Detroit, Mich., USA) was added, mixed well, and then the resulting mixture was intraperitoneally administered to Lewis rats. Dosage was about $1 \times 10^6$ cells/rat. Two weeks and three weeks later, the same suspension was similarly administered. Three days after the final administration, the spleens were extracted, and the spleen cells obtained were cell-fused with mouse myeloma cell line P3×63 Ag8. U. 1 (ATCC CRL 1597) in the similar manner to that described in the following Example 13 to give a group of hybridomas.

The resultant group of hybridomas was cloned by the limiting dilution method similar to that in Example 13, and then the clones of hybridoma producing an antibody binding to epimorphin were selected by the following method. Thus, as a first screening, hybridomas producing a monoclonal antibody which binds to a lysate of the mesenchymal cells cultured in the clumping form according to the above method but not to a lysate of the mesenchymal cells cultured in the monolayer form on a plastic culture Petridish were selected. Furthermore, as a second screening, there were selected the hybridomas which produce a monoclonal antibody being reactive to the band of epimorphin at about 150 K dalton in molecular weight, said band specifically appearing when a sample containing epimorphin used as immunogen was run in a sodium dodecylsulfate-polyacrylamide gel electrophoresis (SDS-PAGE), by means of the Western blot method in which a monoclonal antibody (culture supernatant of hybridoma) and a radio-labelled anti-rat immunoglobulin antibody were sequentially reacted for detection. Detail of the screening method was shown below.

1) First screening:

The antibody reaction was examined according to the dot blot method by using as an antigen a solution which was prepared by culivating fetal mouse dermal cells with DH medium containing 10% fetal bovine serum either in the clumping form or in the monolayer form for 4 days and then dissolving each of the cultures in 2% SDS (sodium dodecylsulfate) solution. Said dot blotting was carried out using Bio-Dot blotter of Bio-Rad Laboratories. and thereby said antigen was adsorbed on a nitro-cellulose membrane. Said nitrocellulose membrane was allowed to react sequentially with hybridoma culture supernatant and HRP (horse radish peroxidase) labelled anti-rat immunoglobulin antibody (second antibody), and finally subjected to coloration by adding a substrate solution containing diaminobenzidine. There were selected the hybridomas which produce an antibody being positive to the dermal cells produced by clumping cultivation and being negative to those produced by monolayer cultivation.

2) Second screening:

The lysate of the dermal cells obtained by clumping cultivation used in 1) was added to a sample solution for SDS-PAGE, boiled for 5 minutes and then subjected to electrophoresis in a 4–20% gradient gel, according to the method of Laemmli et al. [Nature, 227,680 (1970)]. The western blotting was effected by using Model T. C. 808 (Tefco Co., Nagano, Japan) according to the manufacturer's instruction to transfer the proteins in the gel onto a nitrocellulose membrane, and allowing to react said nitrocellulose membrane sequentially with the hybridoma supernatant and $^{125}$I-labelled anti-rat immunoglobulin antibody. Then, there were selected the hybridomas which produce an antibody rendering the band of epimorphin at the position of 150 K dalton by molecular weight markers positive. Thus, there were obtained hybridomas producing the monoclonal antibody of the present invention which has the desired reaction specificity. Furthermore, of these monoclonal antibodies, a monoclonal antibody inhibiting the construction of epithelium when added to an organ culture system, namely a monoclonal antibody recognizing the active site of epimorphin, was selected by the following method. This hybridoma was named clone 12, and the monoclonal antibody was named mAb12. Thus, organ cultivation of the fetal mouse tissues at the stage of active morphogenesis (lung on the 11th day of pregnancy, skin and small intestine on the 13th day of pregnancy) were effected by putting tissue slices of a fetal mouse aseptically removed from an ICR pregnant mouse onto NUCLEOPORE™ membranes (13 mm diameter, 8 μm pore diameter) floating on DH medium containing 10% fetal bovine serum and incubating them. For a half thereof, the incubation was effected in the medium containing 300 μg/ml of the monoclonal antibody which was purified by the method as shown in below b). As a control, those prepared by adding rat IgG, which was purified by the similar method to that for the monoclonal antibody, to a medium at the same concentration were used in parallel. FIG. 1 shows the tissue slice on the 3rd day of organ culture with the monoclonal antibody mAb12. In the control, normal construction (formation of plumonaly alveoli, small intestine plicae etc.) of epithelial structure was found in each organ. To the contrary, in the presence of mAb12, wherein the activity of epimorphin was inhibited, the epithelial tissues were found to become abnormal.

b) Clone 12 obtained in a) above was subcultured in a 1:1 mixed medium (DH) (D8900, Sigma Company) of Dalbecco's modified MEM and Ham F12, containing 12% fetal bovine serum, at 37° C. in a 5% carbon dioxide incubator. Subsequently, the cells were washed twice with serum-free DH and then incubated in serum-free DH for 1 week to give each 6 liter of serum-free and serum-containing DHs containing mAb12. These were salted out with 50% ammonium sulfate, dialyzed against PBS and subjected to affinity purification with anti-rat IgG column (American Qualex International). The antibody adsorbed on the column was eluted with 0.015 N HCl and then neutralized by adding 0.1 M PBS (phosphate buffered saline, pH 8.0). The antibody was further salted out, and then dialyzed against DH thoroughly to give about 5 mg/ml of the purified product.

Example 2. Isolation of Mouse Epimorphin cDNA mRNA prepared from mouse fetal mesenchymal cells was purified on a column of oligo (dT) cellulose (Pharmacia) according to the manufacturer's instruction, and used as a starting material for preparing a cDNA library in λgt11 (Amersham) system according to the protocol (PRN 1280) of Amersham. Thus, the preparation of the cDNA library was effected by inserting cDNA into the EcoRI cleavage site of λgt11 DNA, followed by in vitro packaging to incorporate cDNAs into λ phage particles. Mouse fetal mesenchymal cells used were prepared by removing fetal mice from ICR pregnant mice (purchased from Japan Charles River Co.), subjecting them to trypsin digestion in the presence of calcium in the similar manner to that in Example 1 to isolate the mesenchymal cells and cultivating said cells in the clumping form for 4 days in the similar manner to that described in Example 1. Preparation of mRNA was effected as shown below. The cells were recovered and homogenized in 5.5 M guanidium thiocyanate (GTC) solution with a Polytron-type homogenizer. Cecium trifluoroacetate (CsTFA) –0.1 M EDTA solution was introduced into a centrifuge tube, onto which the above solution was superposed, and then centrifuged at 15° C. at 23,000 rpm for 24 hours to give an RNA pellet. Then, the pellet was dissolved in 4 M GTC solution and centrifuged at 10,000 rpm for 10 minutes to remove the insoluble materials. The supernatant was mixed with 100 μl of 1 M acetic acid and 3 ml of ethanol, allowed to stand at –20° C. for 3 hours, then centrifuged at 10,000 rpm for 20 minutes, and the resultant RNA pellet was dissolved in small amount of TE (Tris-HCl, 10 mM; EDTA, 1 mM) solution. Furthermore, 1/10 fold volume of 1 M Tris (pH 9.0), 1/50 fold volume of 5 M NaCl, 1/20 fold volume of 10% SDS, 1/2 fold volume of phenol (0.1 M Tris-HCl (pH 9.0) saturated) and 1/2 fold volume of chloroform—isoamyl alcohol (24: 1) were added thereto, and the mixture was shaken for 10 minutes and then centrifuged at 3,000 rpm for 10 minutes under cooling to recover an aqueous layer. Furthermore, the same volume of chloroform—isoamyl alcohol was added thereto, and the similar procedure was carried out. At last, 1/10 fold volume of 3 M sodium acetate and 2.5 fold volume of cold ethanol were added, mixed, then allowed to stand still at -20° for 10 hours and centrifuged at 15,000 rpm for 10 minutes to give an RNA pellet. *E. coli* Y1090 (Amersham) infected With said library which had been integrated into λgt11 DNA was plated to form plaques. A nitrocellulose membrane coated with IPTG was then put onto the plate so that IPTG allowed said *E. coli* to synthesize a fused protein between a product of the introduced cDNA and β-galactosidase, said fused protein being concomitantly transferred onto the nitrocellulose membrane. Of the products of the cDNAs adsorbed on the nitrocellulose membrane, a product recognized by the anti-epimorphin antibody obtained in Example 1 was searched by reacting the nitrocellulose membrane sequentially with the anti-epimorphin antibody and anti-rat immunoglobulin antibody labelled with radioactive material for detection, and thereby a λgt11 clone containing a part of the objective epimorphin cDNA was isolated. The cDNA encoding the full length of epimorphin shown as SEQ ID NO: 15 in the Sequence Listing was finally isolated by screening a cDNA library in λgt10 prepared by the similar procedure to that for λgt11 system by means of cDNA cloning system λgt10 (Amersham, PRN. 1257), using as a probe the epimorphin cDNA fragment isolated from the λgt11 obtained.

In the cDNA sequence of SEQ ID NO: 15 in the Sequence Listing, the region actually translated into amino acids is the base sequence from position 153 to position 1019 and the base sequence further containing 3 bases of a termination codon is shown as SEQ ID NO: 12 in the Sequence Listing. SEQ ID NO: 9 in the Sequence Listing shows the protein encoded by this cDNA.

Example 3. Purification of Mouse Epimorphin a) The purified monoclonal antibody mAb12 [5 mg/ml PBS (neutral phosphate buffered physiological saline)] obtained in Example 1 was allowed to react with Affigel 10 (Bio-Rad Laboratories), which has been sequentially washed with isopropanol, 10 mM sodium acetate and PBS, at 4° C. for 5 hours, and thereby immobilized thereon. It was allowed to react with 1 M ethanolamine-HCl (pH 8) for 1 hour to block the unreacted functional groups and then washed with PBS and DH thoroughly to give mAb12-linked Affigel 10.

b) Thirty ICR fetal mice (on the 17th day of pregnancy) were homogenized, washed with PBS, mixed with 20 mM Chaps (Dotire) to solubilize the proteins and a fraction containing epimorphin was extracted. The Affigel 10 prepared in a) was poured into a column, to which the extract was then poured from the top, and incubated at 4° C. overnight. The gel was washed well with PBS. The materials adsorbed on the column was eluted with 15 mM HCl to recover, and subjected to SDS-PAGE electrophoresis, revealing purified epimorphin as shown in FIG. 2.

Example 4. Synthesis of Epimorphin in Animal Cells

Figures 3, 4:
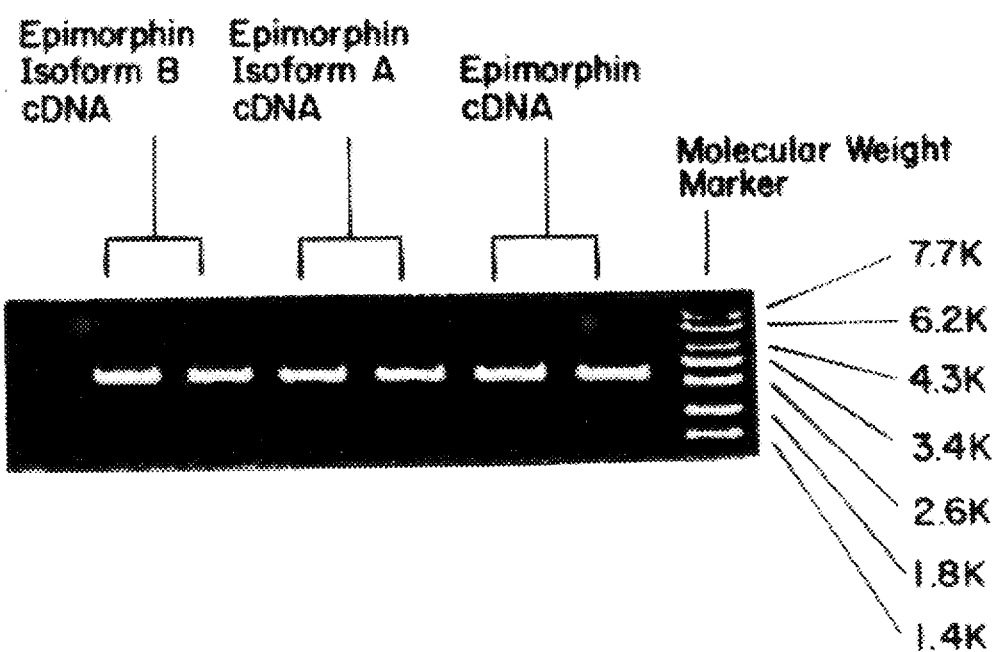
FIG. 3 shows an illustrative Western Blot exhibiting degree of expressions of epimorphin from NIH/3T3 in which epimorphin cDNA has been introduced or not introduced.
FIG. 4 shows the result of the electrophoresis on agarose gel of cDNAs (each in full length) of human epimorphin and human epimorphin Isoforms A and B.

The mouse epimorphin cDNA obtained in Example 2 was incorporated into HindIII-HpaI site of the animal cell expression vector pβactCAT9 [Gene, 48, 1-11 (1986)] having a promotor of β actin, and this expression vector and the hygromycin resistant gene PLSVkmB [Blochlinger et al. Mol. Cell. Biol., 4, 2929–2931 (1984)] were co-introduced into NIH/3T3 cell (ATCC CRT 1658) hardly having endogenous epimorphin activity, by means of cationic liposome lipofection (Gibco). The cells were cultured with DH medium containing hygromycin B (100 µg/ml) and 10% fetal bovine serum for 2 weeks to give the survived transfectants. The cells were dissolved in 2% SDS solution and subjected to SDS-PAGE electrophoresis by the same method as described in Example 1, and the proteins in the gel were transferred onto a nitrocellulose membrane by Western Blot method. The nitrocellulose membrane was sequentially reacted with the monoclonal antibody mAb12 obtained in Example 1 and $^{125}$I-labelled anti-rat immunoglobulin antibody to examine the expression of epimorphin. In consequence, it was confirmed that the resultant transfectants expressed several to several tens fold amount of epimorphin in comparison with non-treated NIH/3T3 (FIG. 3).

Then, the protein expressed was recovered in the similar manner to that in Example 3 to give mouse epimorphin.

Example 5. Isolation of Human Epimorphin cDNA mRNA prepared from human placenta in the similar manner to that described in Example 2 was purified with oligo (dT) cellulose column, and used as a starting material for preparing a cDNA library. The cDNA library was prepared with λgt10 (PRN1257, Amersham) system using λ phage DNA as a vector by the method in which the vector was cut at its EcoRI site into which a cDNA having EcoRI adaptors on the both ends was then incorporated [Huynh, "DNA CLONING", IRL Press (1985)]. This library was allowed to infect *E. coli* NM 514 (Amersham) and plated. Then 12 hours later, the plate was covered with a nylon membrane, onto which cDNAs being replicated within *E. coli* and released from *E. coli* by bacteriolysis were transferred. The DNAs were denatured with 0.5 M-NaOH. By using as a probe a translation region of mouse epimorphin gene obtained in Example 2 which had been labelled with $^{32}$P, a clone containing a fragment of human epimorphin gene hybridizing to said probe was isolated. Finally, by using the human epimorphin fragment so obtained as a probe, said cDNA library was again screened to isolate a cDNA encoding the full length of epimorphin.

The resultant cDNA was a gene which contains the translation region represented by the base sequence shown as SEQ ID NO: 6 in the Sequence Listing, said base sequence encoding human epimorphin having the amino acid sequence of SEQ ID NO: 3 in the Sequence Listing, as well as non-translation region at the 3' and 5' sides, and its full length was found to be about 3.0 kilo base by the agarose gel electrophoresis.

Similarly, there were isolated genes which encode human epimorphin isoforms A and B having the amino acid sequences shown as SEQ ID NOs: 4 and 5 in the Sequence Listing respectively.

These were found to contain, as their translation regions, the base sequences shown as SEQ ID NOs: 7 and 8 in Sequence Listing, respectively, and full lengths thereof were confirmed to be about 2.9 kilo base and 2.8 kilo base, respectively, by the agarose gel electrophoresis (FIG. 4).

The translated protein of the human epimorphin cDNA obtained exhibited almost 90% homology to that of the mouse epimorphin cDNA obtained in Example 2, showing that epimorphin is a substance which has very little difference among species.

Example 6. Isolation of Mouse Epimorphin (Isoforms A, B) cDNAs mRNA prepared from mouse fetal mesenchymal cells in the same manner as that in Example 2 was purified by oligo (dT) cellulose column, and used as a starting material for isolating mouse epimorphin cDNAs in the similar manner to that in Example 5 to give 3 sorts of cDNAs having different lengths. The full lengths thereof by the agarose gel electrophoresis were found to be about 3.0, 2.9 and 2.8 kilo base, respectively. As the result of examining the base sequence of these cDNAs, it was shown that the longest one was consistent with mouse epimorphin obtained in Example 2, and furthermore that, as isoforms of mouse epimorphin, Isoform A of about 2.9 kilo base in full length in which the base sequence from position 942 to position 1066 in SEQ ID NO: 15 in the Sequence Listing had been deleted, and Isoform B of about 2.8 kilo base in full length in which the base sequence from position 942 to position 1127 in SEQ ID NO: 15 in the Sequence Listing had been deleted were cloned. Concerning the former, the part composed of the base sequence from position 153 to position 941 directly bound to the base sequence from position 1067 to position 1141 in SEQ ID NO: 15 in the Sequence Listing is translated into amino acids. SEQ ID NO: 13 in the Sequence Listing shows the base sequence containing 3 bases of a termination codon further to this cDNA sequence, and SEQ ID NO: 10 in the Sequence Listing shows the protein encorded by this cDNA.

Concerning Isoform B, the part composed of the base sequence from position 153 to position 941 directly bound to the base sequence from position 1128 to position 1175 in the SEQ ID NO: 15 in the Sequence Listing is translated into amino acids. SEQ ID NO: 14 in the Sequence Listing shows the base sequence containing 3 bases of a termination codon further to this cDNA sequence, and SEQ ID NO: 11 in the Sequence Listing shows the protein encorded by this cDNA.

For animal species other than mouse and human, their epimorphin cDNAs may be isolated in the similar manner to that in Example 5, using respective animal tissues.

Example 7. Support of Pulmonary Epithelium Structure by Epimorphin

Figure 6:
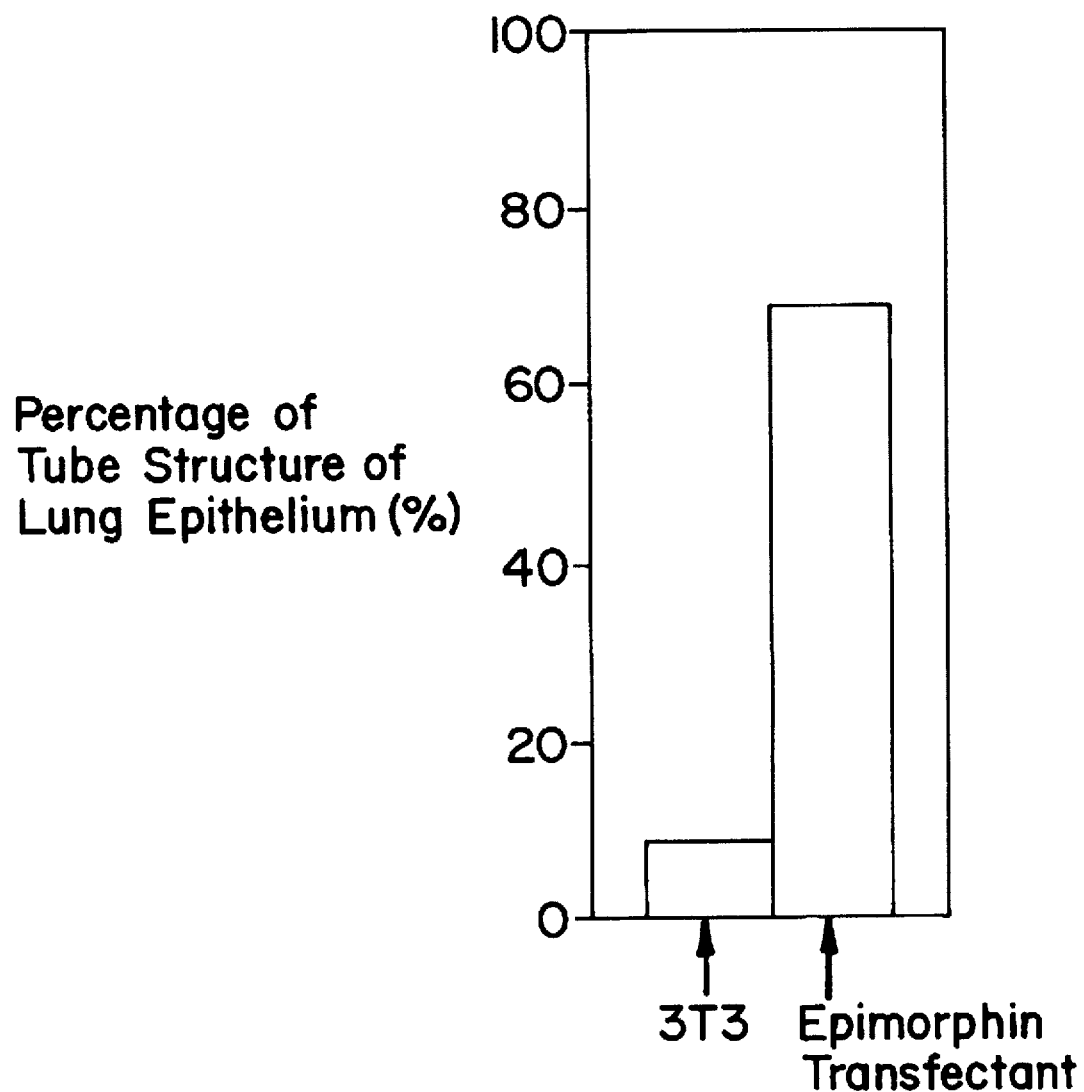
FIG. 6 shows a result of quantitative analysis of the epithelial form as shown in FIG. 5, namely the amount of the epithelium which has grown while retaining the tubular structure on 4th day of culture.

Each of the epimorphin transfectant obtained in Example 4 and non-treated NIH/3T3 cell was mixed with the pulmonary epithelium tissue isolated from fetal mice in the similar manner to that described in Example 1, and subjected to three-dimensional cultivation on nuclepore membranes. When non-treated NIH/3T3 cell was used, the tubular form of pulmonary epithelium was destructed within several days cultivation. To the contrary, the epithelium continued to grow while keeping the form when epimorphin transfectant was used. Thus, it was confirmed that epimorphin plays a very important role in the morphogenesis of epithelial tissue. FIG. 5 shows a photograph of the slice one week after, and FIG. 6 shows the ratio of the epithelium which takes tubular structure.

Example 8. Synthesis of Epimorphin in the Cell-Free System

The human epimorphin cDNA obtained in Example 5 was incorporated into polycloning site of pBluescriptII vector (Stratagene), and the epimorphin mRNA was synthesized by means of In Vitro Eukaryotic Translation Kit (Stratagene) using RNA polymerase and mCAP™ RNA Capping Kit (Stratagene) according to each of the manufacturer's instruction. Then, the human epimorphin labelled with $^{35}$S was synthesized by reacting the resultant mRNA in the presence of $^{35}$S-methionine in the reaction system of Rabbit Reticular Erythrocyte Lysate (Amersham) for 90 minutes.

Figure 7:
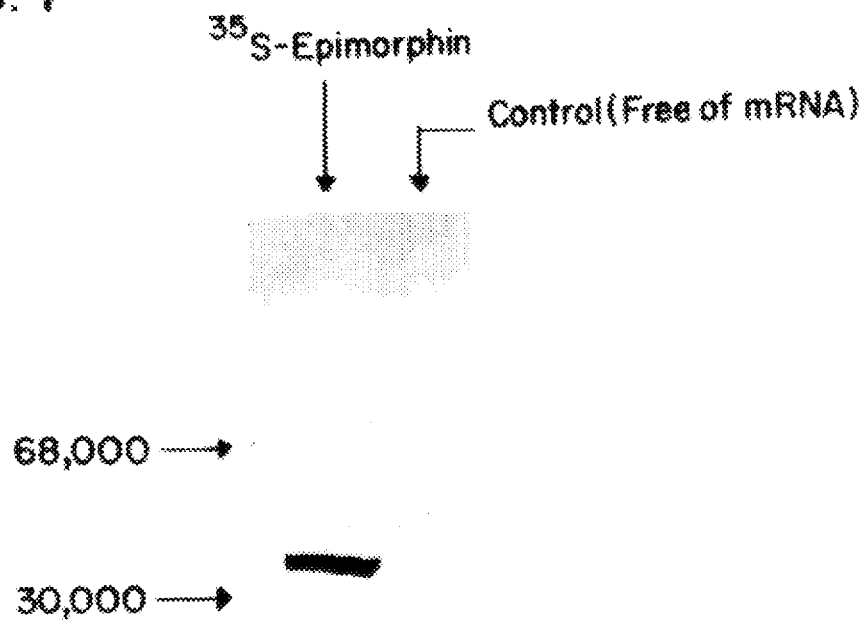
FIG. 7 shows the result of electrophoresis over SDS-PAGE of human epimorphin prepared in a cell-free system.

The synthesized human epimorphin represented by the amino acid sequence of 288 amino acids shown as SEQ ID NO: 3 in the Sequence Listing was confirmed to have a molecular weight of about 33,000 by the SDS-PAGE electrophoresis (FIG. 7).

Similarly, there were obtained human epimorphin Isoforms A and B which are represented by the amino acid sequence of 287 amino acids shown as SEQ ID NO: 4 in the Sequence Listing and the amino acid sequence of 277 amino acids shown as SEQ ID NO: 5 in the Sequence Listing, respectively. It was confirmed by the SDS-PAGE electrophoresis that said human epimorphin Isoforms A and B have molecular weights of about 33,000 and 32,000, respectively.

Example 9. Synthesis of the Soluble Modified Epimorphin Lacking the Hydrophobic Moiety in Animal Cell The mouse epimorphin cDNA obtained in Example 2 was incorporated into the HindIII-HpaI site of the animal cell expression vector pβactCAT9 having a promotor of β-actin in the similar manner to that in Example 4 (βactEPM1).

Figure 8:
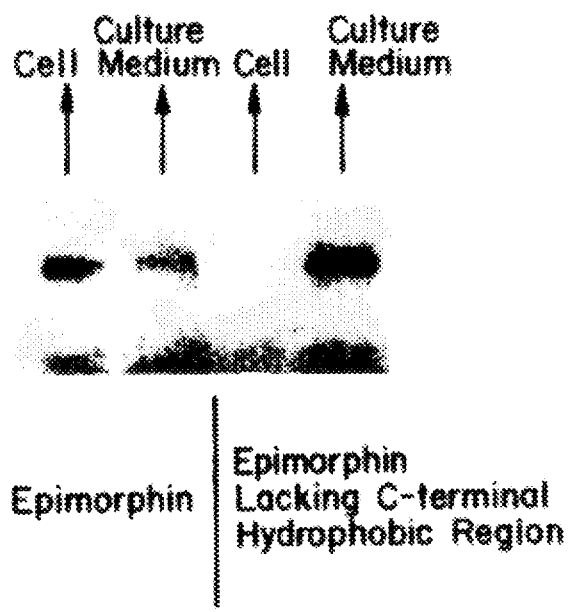
FIG. 8 shows illustrative Western Blot exhibiting the state of expression of epimorphin containing the hydrophobic region at the C-terminal and epimorphin containing no hydrophobic region.

Then, a gene lacking 100% of the moiety encoding the epimorphin C terminal hydrophobic region was prepared by digesting with HincII and NheI, blunt-ending, and religating (βactEPM2). As the result of examining the expressions of epimorphin by introducing βactEPM1 and βactEPM2 into NIH/3T3 cells in the manner described in Example 4, epimorphin was detected mainly on the cell surface in the case of the transfectant containing βactEPM1 and mainly in the culture medium in the case of the transfectant containing βactEPM2, confirming that epimorphin was solubilized in the latter case (FIG. 8).

Each of two kinds of epimorphin transfectant obtained above and the non-treated NIH/3T3 cell was mixed with pulmonary epithelium tissue isolated from fetal mice, and put onto NUCLEOPORE™ membranes to achieve three dimensional cultivation. The tubular form of the pulmonary epithelium was destructed within several days cultivation when the non-treated NIH/3T3 cell was used. To the contrary, alveoli continued to grow with keeping the epithelium form when two kinds of the transfectant were used, confirming that the soluble epimorphin remained active (FIG. 9).

Example 10. Synthesis of the Soluble Modified Epimorphin Lacking the Hydrophobic Moiety in E. coli The mouse epimorphin cDNA obtained in Example 2 was incorporated into pBluescript II KS (+) (Stratagene), and then used to delete the epimorphin gene from its 3' side by making use of a restriction site positioned at the cDNA 3' side, exonuclease III and Mung Bean nuclease so as to create genes having various size. These plasmids were introduced into E. coli JM109 (Takara Shuzoh) to allow, by adding IPTG, the gene product to express as a fused protein with β-galactosidase. In consequence, it was found that the fused protein was easily solubilized by destroying said bacterium in the case of those lacking the gene corresponding to 12 or more amino acids of epimorphin C-terminal hydrophobic regions. Furthermore, it was confirmed that even the epimorphin lacking the amino acids on and after the 231st one from the N-terminus has the epimorphin activity.

Example 11. Synthesis of the Soluble Modified Epimorphin in which the Hydrophobic Region has been Replaced by a Hydrophilic Protein The moiety encoding the C-terminal hydrophobic region of the human epimorphin cDNA obtained in Example 5 was deleted in the similar manner to that in Example 10. Then, CD4 region of the vector CDM8 into which CD4-IgG gene had been incorporated [Romeo and Seed, Cell, 64, 1037–1046 (1991)] was deleted with restriction enzyme, and the cleaved sites of the vector were made blunt-ended. Then, the C-terminus deficient human epimorphin cDNA was inserted into the vector. Among these vectors, one which was in frame, and therefore capable of expressing the cDNA for a fused protein between human epimorphin and IgG Was cloned.

According to the Deae-Dextran method [Current Protocols in Molecular Biology, Wiley Interscience (1987)], a mixture of the vector into which the human epimorphin cDNA has been incorporated and diethylaminoethyl (DEAE)-dextran was incubated in contact with culture cells to introduce the vector into COS-1 cell (ATCC CRL 1650). Three days later, the culture medium was recovered. The culture medium was salted out with 50% ammonium sulfate to be concentrated. Then, by using a column filled with carriers onto which Protein A having a binding ability to IgG has been conjugated (Takara Shuzoh Company), a large amount of the human epimorphin-IgG fused protein in which the C-terminal hydrophobic residues had been replaced by a hydrophilic peptide was recovered as a purified product.

It was confirmed that said modified human epimorphin was highly soluble and had the epimorphin activity.

Modified epimorphins of other animal species may also be obtained by using the respective epimorphin cDNAs in the similar manner to those in Examples 9–11.

Example 12. Preparation of Polyclonal Antibody Against Epimorphin a) The soluble human epimorphin-β galactosidase fused protein was produced in *E. coli* in the similar manner to that in Example 10, using the human epimorphin cDNA obtained in Example 5. A solution was separated from a suspension (lysate) obtained by destructing *E. coli*, subjected to SDS-PAGE. Then, the gel was subjected to protein staining. The band corresponding to the soluble human epimorphin-β galactosidase fused protein was cut out to give a solution of the highly pure human epimorphin-β galactosidase fused protein.

b) The solution of the soluble human epimorphin-β galactosidase fused protein obtained in a) was mixed with an equal amount of Freund complete adjuvant, and the resultant suspension was intraperitoneally administered to Lewis rats. Two weeks and 3 weeks later, the same suspension was similarly administered. Three days after the final administration, blood was taken from the rats, and the serum was separated conventionally to give antiserum against human epimorphin. For examining the activity of the antiserum, the dot blot method in which the soluble human epimorphin-β galactosidase fused protein used as an immunogen was adsorbed onto a nitrocellulose membrane, allowed to react sequentially with stepwise diluted antiserum and enzyme-labelled anti-rat immunoglobulin antibody and finally mixed with a coloring substrate solution, was used. Furthermore, said antiserum was salted out with 50% ammonium sulfate, dialyzed against PBS and then affinity purified with anti-rat IgG column (American Qualex International) to give polyclonal antibody against human epimorphin. Although said polyclonal antibody contains antibodies against β-galactosidase, it can be used as such when used for mammal experiments. Said polyclonal antibody bound specifically to human epimorphin and also to those of other animal species such as mouse, chicken and the like.

Example 13. Preparation of Monoclonal Antibody Against Epimorphin

The mouse epimorphin obtained in Example 3 was mixed with an equal amount of Freund complete adjuvant, and the resultant suspension was intraperitoneally administered to a Lewis rat. Two weeks and three weeks later, the same suspension was similarly administered. Three days after the final administration, the spleen was removed, and the splenic cells were washed three times with 1:1 mixed medium (DH) of Dalbecco's modified MEM and Ham F12. Mouse myeloma cell line P3×63Ag8. U. 1 (ATCC CRL 1597) was washed similarly, and $1 \times 10^7$ cells of said cell line and $1 \times 10^8$ cells of said splenic cells were put into a 50 ml centrifuge tube and mixed. After centrifugation at 200×G for 5 minutes, the supernatant was removed with a Pastur pipette. Then 1 ml of RPMI-1640 solution containing 50% (w/v) polyethylene glycol 1500 (Boehringer-Mannheim Yamanouchi) kept at 37° C. was added dropwise over 1 minute to the cell pellet, with mixing. Then, 1 ml of RPMI-1640 solution kept at 37° C. was added and the mixture was allowed to stand still for 1 minute. Then, 2 ml of the same solution was added, and the mixture was allowed to stand still for 2 minutes, followed by addition of 1 ml of the same solution. After standing still for 4 minutes, 8 ml of DH kept at 37° C. containing 12% fetal bovine serum, 0.05 g titer/1-streptomycin sulfate and 60,000 U/1-penicillin G potassium (hereinafter referred to as "DH 12") was added, and then centrifuged at 200×G for 5 minutes. The supernatant was removed. The cells were suspended in DH 12 kept at 37° C. to $1 \times 10^6$ splenic cells/ml, and each 1 ml aliquot of the suspension was put onto 24-well microplates (Coaster) and incubated at 37° C. in a 5% carbon dioxide incubator.

24 hours later, 1 ml of serum-containing complete RPMI-1640 medium containing $1.0 \times 10^{-4}$ M hypoxanthine, $4.0 \times 10^{-7}$ M aminopterin and $1.6 \times 10^{-5}$ M thymidine (hereinafter referred to as "HAT" medium) was added to each well. A half of the supernatant was replaced by fresh HAT medium on the 2nd, 3rd and 4th days, and on 6th day similarly a half of the supernatant was replaced by serum-containing complete RPMI-1640 medium containing $1.0 \times 10^{-4}$ M hypoxanthine and $1.6 \times 10^{-5}$ M thymidine (HT medium). Hereafter, the culture was maintained in propagation with DH 12.

Hybridomas thus obtained were subjected to cloning by limiting dilution method. Thus, 20 ml of DH 12 medium adjusted so as to contain $3 \times 10^2$ hybridomas and $1 \times 10^8$ Balb/c mouse thymocytes was used to put onto 96-well plates so as to achieve 3 hybridomas/well, and incubated. The propagating hybridoma was cloned similarly by plating at 1 hybridoma/well, and the further propagating hybridoma was cloned similarly by plating at 0.3 hybridomas/well.

Selection of the clone producing the objective antibody was effected by determining the binding ability of the antibody to mouse epimorphin according to the ELISA method. Thus, each 50 μl aliquot of the solution of the soluble mouse epimorphin obtained in Example 10 was poured into 96-well Immunoplates (Nunc Intermed), allowed to stand still at 4° C. overnight, and the wells were washed with PBS-0.05% Tween 20 (washing solution). As blocking liquid, 100 microliter/well of PBS-5% skim milk solution was added, allowed to stand still at room temperature for 1 hour and the wells were washed with the washing solution. Culture supernatant of hybridoma and a horse radish peroxidase-labelled anti-rat immunoglobulin solution (Cappel) were sequentially added in volume of 50 microliter/well, allowed to react at room temperature for 1 hour and then the wells were washed with the washing solution. At last, 100 microliter/well of a customarily used substrate solution containing o-phenylenediamine and hydrogen peroxide was added, subjected to the coloring reaction for 15 minutes, and then the reaction was stopped with sulfuric acid solution, and the absorbance at 492 nm was measured. The culture supernatant of the hybridoma producing the objective monoclonal antibody showed above 3-fold higher absorbance than the culture medium not used yet (negative control).

Thus, there has been obtained the hybridoma producing a monoclonal antibody which binds to the site other than the active site of mouse epimorphin. From the culture supernatant of this hybridoma, the monoclonal antibody binding to the site other than the active site of mouse epimorphin was purified in the similar manner to that described in Example 1.

Example 14. Examination of the Expression of Epimorphin Using a Monoclonal Antibody Against Epimorphin Lungs, skins and small intestines of fetal and adult mice were removed, fixed with 4% paraformaldehyde, and then freezed samples were prepared using embedding agents. Slices in 10 micrometer thick were prepared using cryostat, dried, and then allowed to react sequentially with PBS containing 5% skim milk, 100 fold-diluted monoclonal antibody mAb12 solution obtained in Example 1 and anti-rat immunoglobulin antibody labelled by fluorescein isothiocyanate (FITC) (Tago) to achieve fluorescent immunostaining, and the expression patterns of epimorphin were examined using a fluorescence microscope. Further, the slices were washed sufficiently with PBS in the intervals of the above reactions to inhibit non-specific adsorption of the antibodies. As shown in FIG. 10, it was confirmed that the expression amounts of epimorphin increase at the fetal stage and at the regenerating stage of organs of the adult animal.

As explained above, epimorphin of the present invention as such is useful for developing therapeutic agents to congenital disorders of epithelial forms as well as acquired disorders of epithelial forms such as alopecia, lesion of various organs, etc, since it is a mesenchymal ingredient having morphogenetic effect of epithelial tissues. In particular, epimorphins modified to be soluble are easily purified and advantageously available as a solution of desired concentration.

Furthermore, the gene encoding epimorphin enables to produce epimorphin in a large scale and is very useful for diagnosis of said diseases or disorders and for developing therapeutic methods therefor.

Furthermore, the antibody against epimorphin is also very useful for purification of epimorphin, detection of epimorphin, and diagnosis of said diseases or disorders and for developing therapeutic methods therefor.

What is claimed is:

1. An isolated human mesenchyme polypeptide capable of effecting eipthelial morphogenesis in mammals, comprising the N-terminal sequence shown in SEQ ID NO: 2 and having a molecular weight of about 70 KD as determined by SDS-PAGE gel.

2. An isolated murine mesenchyme polypeptide capable of effecting epithelial morphogenesis in mammals, comprising the N-terminal sequence shown in SEQ ID NO: 2 and having a molecular weight of about 150 KD as determined by SDS-PAGE gel.

3. An isolated human mesenchyme polypeptide capable of effecting eipthelial morphogenesis in mammals, comprising the N-terminal sequence shown in SEQ ID NO: 2 and having a molecular weight of between 32–33 kD as determined by SDS-PAGE gel, when synthesized in a cell-free system.

4. An isolated mouse mesenchyme polypeptide capable of effecting eipthelial morphogenesis in mammals, comprising the N-terminal sequence shown in SEQ. ID NO: 2 and having a molecular weight of between 32–33 kD as determined by SDS-PAGE gel, when synthesized in a cell-free system.

5. An isolated and purified polypeptide capable of effecting epithelial morphogenesis in mammals, comprising one of the amino acid sequences set forth in SEQ ID NO: 3, 4 or 5.

6. An isolated DNA molecule encoding the polypeptide of claim 5.

7. The DNA molecule according to claim 6, comprising one of the sequences set forth in SEQ ID NO: 6, 7 or 8.

8. An isolated and purified polypeptide capable of effecting epithelial morphogenesis in mammals, comprising one of the amino acid sequences set forth in SEQ ID NO: 9, 10 or 11.

9. An isolated DNA molecule encoding the polypeptide of claim 8.

10. The DNA molecule according to claim 9, comprising one of the sequences set forth in SEQ ID NO: 12, 13 or 14.

11. An isolated polypeptide capable of effecting epithelial morphogenesis in mammals, comprising amino acids 1 to 230 of SEQ ID NO: 3, 4 or 5.

12. The polypeptide according to claim 11, which further comprises a non-hydrophobic polypeptide connected to its C-terminus.

13. An isolated polypeptide capable of effecting epithelial morphogenesis in mammals, comprising amino acids 1 to 230 of SEQ ID NO: 9, 10 or 11.

14. The polypeptide according to claim 13, which further comprises a non-hydrophobic polypeptide connected to its C-terminus.

* * * * *

UNITED STATES PATENT AND TRADEMARK OFFICE
CERTIFICATE OF CORRECTION

PATENT NO. : 5,726,298
DATED : March 10, 1998
INVENTOR(S) : Hirai, et al

It is certified that error appears in the above-indentified patent and that said Letters Patent is hereby corrected as shown below:

On the title page:

Please change "[73] Assignee: Biomedical Research Institute Co., Ltd."

to --[73] Assignee: Biomaterial Research Institute Co., Ltd.--.

Signed and Sealed this

Nineteenth Day of October, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 36
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

ATG CGG GAC CGG CTG CCA GAC CTG ACG GCG TGT AGG    36

( 2 ) INFORMATION FOR SEQ ID NO:2:

( i ) SEQUENCE CHARACTERISTICS:
        ( A ) LENGTH: 11
        ( B ) TYPE: amino acid
        ( D ) TOPOLOGY: linear ( i i ) MOLECULE TYPE: peptide ( x i ) SEQUENCE DESCRIPTION: SEQ ID NO:2:

Met Arg Asp Arg Leu Pro Asp Leu Thr Ala Cys ( 2 ) INFORMATION FOR SEQ ID NO:3:

( i ) SEQUENCE CHARACTERISTICS:
        ( A ) LENGTH: 288
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Met Arg Asp Arg Leu Pro Asp Leu Thr Ala Cys Arg Lys Asn Asp Asp
              5                  10                      15
Gly Asp Thr Val Val Val Glu Lys Asp His Phe Met Asp Asp Phe
         20              25                  30
Phe His Gln Val Glu Glu Ile Arg Asn Ser Ile Asp Lys Ile Thr Gln
         35              40                  45
Tyr Val Glu Glu Val Lys Lys Asn His Ser Ile Ile Leu Ser Ala Pro
     50              55                  60
Asn Pro Glu Gly Lys Ile Lys Glu Glu Leu Glu Asp Leu Asn Lys Glu
65                  70              75                      80
Ile Lys Lys Thr Ala Asn Lys Ile Arg Ala Lys Leu Lys Ala Ile Glu
                 85              90                      95
Gln Ser Phe Asp Gln Asp Glu Ser Gly Asn Arg Thr Ser Val Asp Leu
             100              105                 110
Arg Ile Arg Arg Thr Gln His Ser Val Leu Ser Arg Lys Phe Val Glu
         115              120                 125
Ala Met Ala Glu Tyr Asn Glu Ala Gln Thr Leu Phe Arg Glu Arg Ser
     130              135                 140
Lys Gly Arg Ile Gln Arg Gln Leu Glu Ile Thr Gly Arg Thr Thr Thr
145                  150              155                 160
Asp Asp Glu Leu Glu Glu Met Leu Glu Ser Gly Lys Pro Ser Ile Phe
                 165              170                 175
Thr Ser Asp Ile Ile Ser Asp Ser Gln Ile Thr Arg Gln Ala Leu Asn
             180              185                 190
Glu Ile Glu Ser Arg His Lys Asp Ile Met Lys Leu Glu Thr Ser Ile
         195              200                 205
Arg Glu Leu His Glu Met Phe Met Asp Met Ala Met Phe Val Glu Thr
     210              215                 220
Gln Gly Glu Met Ile Asn Asn Ile Glu Arg Asn Val Met Asn Ala Thr
225                  230              235                 240
Asp Tyr Val Glu His Ala Lys Glu Glu Thr Lys Lys Ala Ile Lys Tyr
                 245              250                 255
Gln Ser Lys Ala Arg Arg Lys Lys Trp Ile Ile Ile Ala Val Ser Val
             260              265                 270
Val Leu Val Val Ile Ile Val Leu Ile Ile Gly Leu Ser Val Gly Lys
         275              280                 285
```

( 2 ) INFORMATION FOR SEQ ID NO:4:

( i ) SEQUENCE CHARACTERISTICS:
        ( A ) LENGTH: 287
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Met Arg Asp Arg Leu Pro Asp Leu Thr Ala Cys Arg Lys Asn Asp Asp
              5                  10                      15
```

```
Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
        50                  55                  60

Asn Pro Glu Gly Lys Ile Lys Glu Glu Leu Glu Asp Leu Asn Lys Glu
65                      70                  75                  80

Ile Lys Lys Thr Ala Asn Lys Ile Arg Ala Lys Leu Lys Ala Ile Glu
                85                  90                          95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
        130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Leu Met Phe Ile Ile Ile Cys Val Ile
            260                 265                 270

Val Leu Leu Val Ile Leu Gly Ile Ile Leu Ala Thr Thr Leu Ser
        275                 280                 285
```

( 2 ) INFORMATION FOR SEQ ID NO:5:

( i ) SEQUENCE CHARACTERISTICS:
        ( A ) LENGTH: 277
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Met Arg Asp Arg Leu Pro Asp Leu Thr Ala Cys Arg Lys Asn Asp Asp
                5                   10                  15

Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
        50                  55                  60

Asn Pro Glu Gly Lys Ile Lys Glu Glu Leu Glu Asp Leu Asn Lys Glu
65                      70                  75                  80

Ile Lys Lys Thr Ala Asn Lys Ile Arg Ala Lys Leu Lys Ala Ile Glu
```

|        |     |     |     | 85  |     |     |     |     | 90  |     |     |     |     | 95  |     |
|--------|-----|-----|-----|-----|-----|-----|-----|-----|-----|-----|-----|-----|-----|-----|-----|
| Gln | Ser | Phe | Asp | Gln | Asp | Glu | Ser | Gly | Asn | Arg | Thr | Ser | Val | Asp | Leu |
|     |     |     | 100 |     |     |     |     | 105 |     |     |     | 110 |     |     |     |

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Gln Gln His Cys His Ser Asn His Ile Pro
            260                 265                 270

Arg Ala Ile Tyr Pro
            275

( 2 ) INFORMATION FOR SEQ ID NO:6:

( i ) SEQUENCE CHARACTERISTICS:
        ( A ) LENGTH: 867
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
ATG CGG GAC CGG CTG CCA GAC CTG ACG GCG TGT AGG AAG AAT GAT GAT    48
GGA GAC ACA GTT GTT GTG GTT GAG AAA GAT CAT TTC ATG GAT GAT TTC    96
TTC CAT CAG GTG GAG GAG ATT AGA AAC AGT ATT GAT AAA ATA ACT CAA   144
TAT GTT GAA GAA GTA AAG AAA AAC CAC AGC ATC ATT CTT TCT GCA CCA   192
AAC CCG GAA GGA AAA ATA AAA GAA GAG CTT GAA GAT CTG AAC AAA GAA   240
ATC AAG AAA ACT GCG AAT AAA ATT CGA GCC AAG TTA AAG GCT ATT GAA   288
CAA AGT TTT GAT CAG GAT GAG AGT GGG AAC CGG ACT TCA GTG GAT CTT   336
CGG ATA CGA AGA ACC CAG CAT TCG GTG CTG TCT CGG AAG TTT GTG GAA   384
GCC ATG GCG GAG TAC AAT GAG GCA CAG ACT CTG TTT CGG GAG CGG AGC   432
AAA GGC CGC ATC CAG CGC CAG CTG GAG ATA ACT GGG AGA ACC ACC ACA   480
GAC GAC GAG CTA GAA GAG ATG CTG GAG AGC GGG AAG CCA TCC ATC TTC   528
ACT TCC GAC ATT ATA TCA GAT TCA CAA ATT ACT AGA CAA GCT CTC AAT   576
GAA ATC GAG TCA CGT CAC AAG GAC ATC ATG AAG CTG GAG ACC AGC ATC   624
CGA GAG TTG CAT GAG ATG TTC ATG GAC ATG GCT ATG TTT GTG GAG ACT   672
CAG GGT GAA ATG ATC AAC AAC ATA GAA AGA AAT GTT ATG AAT GCC ACA   720
```

```
GAC  TAT  GTA  GAA  CAC  GCT  AAA  GAA  GAA  ACA  AAA  AAA  GCT  ATC  AAA  TAT   768
CAG  AGC  AAG  GCA  AGA  AGG  AAA  AAG  TGG  ATA  ATT  ATT  GCT  GTG  TCA  GTG   816
GTT  CTG  GTT  GTC  ATA  ATC  GTT  CTA  ATT  ATT  GGC  TTG  TCA  GTT  GGC  AAA   864
TGA                                                                               867
```

( 2 ) INFORMATION FOR SEQ ID NO:7:

( i ) SEQUENCE CHARACTERISTICS:
        ( A ) LENGTH: 864
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
ATG  CGG  GAC  CGG  CTG  CCA  GAC  CTG  ACG  GCG  TGT  AGG  AAG  AAT  GAT  GAT    48
GGA  GAC  ACA  GTT  GTT  GTG  GTT  GAG  AAA  GAT  CAT  TTC  ATG  GAT  GAT  TTC    96
TTC  CAT  CAG  GTG  GAG  GAG  ATT  AGA  AAC  AGT  ATT  GAT  AAA  ATA  ACT  CAA   144
TAT  GTT  GAA  GAA  GTA  AAG  AAA  AAC  CAC  AGC  ATC  ATT  CTT  TCT  GCA  CCA   192
AAC  CCG  GAA  GGA  AAA  ATA  AAA  GAA  GAG  CTT  GAA  GAT  CTG  AAC  AAA  GAA   240
ATC  AAG  AAA  ACT  GCG  AAT  AAA  ATT  CGA  GCC  AAG  TTA  AAG  GCT  ATT  GAA   288
CAA  AGT  TTT  GAT  CAG  GAT  GAG  AGT  GGG  AAC  CGG  ACT  TCA  GTG  GAT  CTT   336
CGG  ATA  CGA  AGA  ACC  CAG  CAT  TCG  GTG  CTG  TCT  CGG  AAG  TTT  GTG  GAA   384
GCC  ATG  GCG  GAG  TAC  AAT  GAG  GCA  CAG  ACT  CTG  TTT  CGG  GAG  CGG  AGC   432
AAA  GGC  CGC  ATC  CAG  CGC  CAG  CTG  GAG  ATA  ACT  GGG  AGA  ACC  ACC  ACA   480
GAC  GAC  GAG  CTA  GAA  GAG  ATG  CTG  GAG  AGC  GGG  AAG  CCA  TCC  ATC  TTC   528
ACT  TCC  GAC  ATT  ATA  TCA  GAT  TCA  CAA  ATT  ACT  AGA  CAA  GCT  CTC  AAT   576
GAA  ATC  GAG  TCA  CGT  CAC  AAG  GAC  ATC  ATG  AAG  CTG  GAG  ACC  AGC  ATC   624
CGA  GAG  TTG  CAT  GAG  ATG  TTC  ATG  GAC  ATG  GCT  ATG  TTT  GTG  GAG  ACT   672
CAG  GGT  GAA  ATG  ATC  AAC  AAC  ATA  GAA  AGA  AAT  GTT  ATG  AAT  GCC  ACA   720
GAC  TAT  GTA  GAA  CAC  GCT  AAA  GAA  GAA  ACA  AAA  AAA  GCT  ATC  AAA  TAT   768
CAG  AGC  AAG  GCA  AGA  AGG  AAA  TTG  ATG  TTC  ATT  ATT  ATT  TGT  GTA  ATT   816
GTT  TTG  CTT  GTG  ATC  CTT  GGA  ATT  ATC  CTA  GCA  ACA  ACA  TTG  TCA  TAG   864
```

( 2 ) INFORMATION FOR SEQ ID NO:8:

( i ) SEQUENCE CHARACTERISTICS:
        ( A ) LENGTH: 834
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

```
ATG  CGG  GAC  CGG  CTG  CCA  GAC  CTG  ACG  GCG  TGT  AGG  AAG  AAT  GAT  GAT    48
GGA  GAC  ACA  GTT  GTT  GTG  GTT  GAG  AAA  GAT  CAT  TTC  ATG  GAT  GAT  TTC    96
TTC  CAT  CAG  GTG  GAG  GAG  ATT  AGA  AAC  AGT  ATT  GAT  AAA  ATA  ACT  CAA   144
TAT  GTT  GAA  GAA  GTA  AAG  AAA  AAC  CAC  AGC  ATC  ATT  CTT  TCT  GCA  CCA   192
AAC  CCG  GAA  GGA  AAA  ATA  AAA  GAA  GAG  CTT  GAA  GAT  CTG  AAC  AAA  GAA   240
```

```
ATC AAG AAA ACT GCG AAT AAA ATT CGA GCC AAG TTA AAG GCT ATT GAA   288
CAA AGT TTT GAT CAG GAT GAG AGT GGG AAC CGG ACT TCA GTG GAT CTT   336
CGG ATA CGA AGA ACC CAG CAT TCG GTG CTG TCT CGG AAG TTT GTG GAA   384
GCC ATG GCG GAG TAC AAT GAG GCA CAG ACT CTG TTT CGG GAG CGG AGC   432
AAA GGC CGC ATC CAG CGC CAG CTG GAG ATA ACT GGG AGA ACC ACC ACA   480
GAC GAC GAG CTA GAA GAG ATG CTG GAG AGC GGG AAG CCA TCC ATC TTC   528
ACT TCC GAC ATT ATA TCA GAT TCA CAA ATT ACT AGA CAA GCT CTC AAT   576
GAA ATC GAG TCA CGT CAC AAG GAC ATC ATG AAG CTG GAG ACC AGC ATC   624
CGA GAG TTG CAT GAG ATG TTC ATG GAC ATG GCT ATG TTT GTG GAG ACT   672
CAG GGT GAA ATG ATC AAC AAC ATA GAA AGA AAT GTT ATG AAT GCC ACA   720
GAC TAT GTA GAA CAC GCT AAA GAA GAA ACA AAA AAA GCT ATC AAA TAT   768
CAG AGC AAG GCA AGA AGG CAA CAA CAT TGT CAT AGC AAC CAT ATC CCA   816
AGA GCC ATT TAT CCT TGA                                           834
```

(2) INFORMATION FOR SEQ ID NO:9:

(i) SEQUENCE CHARACTERISTICS:
        (A) LENGTH: 289
        (B) TYPE: amino acid
        (D) TOPOLOGY: linear (ii) MOLECULE TYPE: peptide (xi) SEQUENCE DESCRIPTION: SEQ ID NO:9:

```
Met Arg Asp Arg Leu Pro Asp Leu Thr Ala Cys Arg Thr Asn Asp Asp
 1               5                  10                  15

Gly Asp Thr Ala Val Val Ile Val Glu Lys Asp His Phe Met Asp Gly
             20                  25                  30

Phe Phe His Gln Val Glu Glu Ile Arg Ser Ser Ile Ala Arg Ile Ala
         35                  40                  45

Gln His Val Glu Asp Val Lys Lys Asn His Ser Ile Ile Leu Ser Ala
     50                  55                  60

Pro Asn Pro Glu Gly Lys Ile Lys Glu Glu Leu Glu Asp Leu Asp Lys
 65                  70                  75                  80

Glu Ile Lys Lys Thr Ala Asn Arg Ile Arg Gly Lys Leu Lys Ser Ile
                 85                  90                  95

Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
        115                 120                 125

Asp Val Met Thr Glu Tyr Asn Glu Ala Gln Ile Leu Phe Arg Glu Arg
    130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
    210                 215                 220
```

```
Thr  Gln  Gly  Glu  Met  Val  Asn  Asn  Ile  Glu  Arg  Asn  Val  Val  Asn  Ser
225                      230                      235                           240

Val  Asp  Tyr  Val  Glu  His  Ala  Lys  Glu  Glu  Thr  Lys  Lys  Ala  Ile  Lys
                    245                      250                           255

Tyr  Gln  Ser  Lys  Ala  Arg  Arg  Lys  Lys  Trp  Ile  Ile  Ala  Ala  Val  Ala
               260                      265                      270

Val  Ala  Val  Ile  Ala  Val  Leu  Ala  Leu  Ile  Ile  Gly  Leu  Ser  Val  Gly
          275                      280                      285

Lys
```

( 2 ) INFORMATION FOR SEQ ID NO:10:

( i ) SEQUENCE CHARACTERISTICS:
        ( A ) LENGTH: 288
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Met  Arg  Asp  Arg  Leu  Pro  Asp  Leu  Thr  Ala  Cys  Arg  Thr  Asn  Asp  Asp
1                   5                        10                           15

Gly  Asp  Thr  Ala  Val  Val  Ile  Val  Glu  Lys  Asp  His  Phe  Met  Asp  Gly
               20                       25                       30

Phe  Phe  His  Gln  Val  Glu  Glu  Ile  Arg  Ser  Ser  Ile  Ala  Arg  Ile  Ala
          35                       40                       45

Gln  His  Val  Glu  Asp  Val  Lys  Lys  Asn  His  Ser  Ile  Ile  Leu  Ser  Ala
     50                       55                       60

Pro  Asn  Pro  Glu  Gly  Lys  Ile  Lys  Glu  Glu  Leu  Glu  Asp  Leu  Asp  Lys
65                       70                       75                           80

Glu  Ile  Lys  Lys  Thr  Ala  Asn  Arg  Ile  Arg  Gly  Lys  Leu  Lys  Ser  Ile
               85                       90                       95

Glu  Gln  Ser  Cys  Asp  Gln  Asp  Glu  Asn  Gly  Asn  Arg  Thr  Ser  Val  Asp
               100                      105                      110

Leu  Arg  Ile  Arg  Arg  Thr  Gln  His  Ser  Val  Leu  Ser  Arg  Lys  Phe  Val
          115                      120                      125

Asp  Val  Met  Thr  Glu  Tyr  Asn  Glu  Ala  Gln  Ile  Leu  Phe  Arg  Glu  Arg
     130                      135                      140

Ser  Lys  Gly  Arg  Ile  Gln  Arg  Gln  Leu  Glu  Ile  Thr  Gly  Arg  Thr  Thr
145                      150                      155                           160

Thr  Asp  Asp  Glu  Leu  Glu  Glu  Met  Leu  Glu  Ser  Gly  Lys  Pro  Ser  Ile
               165                      170                      175

Phe  Ile  Ser  Asp  Ile  Ile  Ser  Asp  Ser  Gln  Ile  Thr  Arg  Gln  Ala  Leu
               180                      185                      190

Asn  Glu  Ile  Glu  Ser  Arg  His  Lys  Asp  Ile  Met  Lys  Leu  Glu  Thr  Ser
          195                      200                      205

Ile  Arg  Glu  Leu  His  Glu  Met  Phe  Met  Asp  Met  Ala  Met  Phe  Val  Glu
     210                      215                      220

Thr  Gln  Gly  Glu  Met  Val  Asn  Asn  Ile  Glu  Arg  Asn  Val  Val  Asn  Ser
225                      230                      235                           240

Val  Asp  Tyr  Val  Glu  His  Ala  Lys  Glu  Glu  Thr  Lys  Lys  Ala  Ile  Lys
                    245                      250                           255

Tyr  Gln  Ser  Lys  Ala  Arg  Arg  Lys  Val  Met  Phe  Val  Leu  Ile  Cys  Val
               260                      265                      270

Val  Thr  Leu  Leu  Val  Ile  Leu  Gly  Ile  Ile  Leu  Ala  Thr  Ala  Leu  Ser
          275                      280                      285
```

( 2 ) INFORMATION FOR SEQ ID NO:11:

( i ) SEQUENCE CHARACTERISTICS:
        ( A ) LENGTH: 279
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Met Arg Asp Arg Leu Pro Asp Leu Thr Ala Cys Arg Thr Asn Asp Asp
 1               5                  10                  15
Gly Asp Thr Ala Val Val Ile Val Glu Lys Asp His Phe Met Asp Gly
            20                  25                  30
Phe Phe His Gln Val Glu Glu Ile Arg Ser Ser Ile Ala Arg Ile Ala
        35                  40                  45
Gln His Val Glu Asp Val Lys Lys Asn His Ser Ile Ile Leu Ser Ala
    50                  55                  60
Pro Asn Pro Glu Gly Lys Ile Lys Glu Glu Leu Glu Asp Leu Asp Lys
65                  70                  75                  80
Glu Ile Lys Lys Thr Ala Asn Arg Ile Arg Gly Lys Leu Lys Ser Ile
                85                  90                  95
Glu Gln Ser Cys Asp Gln Asp Glu Asn Gly Asn Arg Thr Ser Val Asp
            100                 105                 110
Leu Arg Ile Arg Arg Thr Gln His Ser Val Leu Ser Arg Lys Phe Val
        115                 120                 125
Asp Val Met Thr Glu Tyr Asn Glu Ala Gln Ile Leu Phe Arg Glu Arg
    130                 135                 140
Ser Lys Gly Arg Ile Gln Arg Gln Leu Glu Ile Thr Gly Arg Thr Thr
145                 150                 155                 160
Thr Asp Asp Glu Leu Glu Glu Met Leu Glu Ser Gly Lys Pro Ser Ile
                165                 170                 175
Phe Ile Ser Asp Ile Ile Ser Asp Ser Gln Ile Thr Arg Gln Ala Leu
            180                 185                 190
Asn Glu Ile Glu Ser Arg His Lys Asp Ile Met Lys Leu Glu Thr Ser
        195                 200                 205
Ile Arg Glu Leu His Glu Met Phe Met Asp Met Ala Met Phe Val Glu
    210                 215                 220
Thr Gln Gly Glu Met Val Asn Asn Ile Glu Arg Asn Val Val Asn Ser
225                 230                 235                 240
Val Asp Tyr Val Glu His Ala Lys Glu Glu Thr Lys Lys Ala Ile Lys
                245                 250                 255
Tyr Gln Ser Lys Ala Arg Arg Gln Gln His Cys His Ser Asn Arg Thr
            260                 265                 270
Pro Arg Ala Leu Cys Pro Arg
            275
```

( 2 ) INFORMATION FOR SEQ ID NO:12:

( i ) SEQUENCE CHARACTERISTICS:
        ( A ) LENGTH: 870
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:12:

-continued

```
ATG CGG GAC CGG CTG CCC GAC CTC ACG GCG TGT AGG ACA AAC GAC GAT    48
GGA GAC ACT GCT GTC GTC ATT GTG GAG AAG GAT CAT TTC ATG GAC GGT    96
TTC TTC CAT CAG GTA GAG GAG ATT CGA AGC AGC ATA GCC AGG ATT GCT   144
CAG CAT GTA GAA GAC GTG AAG AAG AAC CAC AGC ATC ATC CTG TCT GCT   192
CCA AAC CCA GAA GGA AAA ATA AAA GAA GAG CTG GAG GAC CTG GAC AAA   240
GAG ATC AAG AAA ACT GCT AAC AGG ATC CGG GGC AAG CTG AAG TCT ATT   288
GAG CAG AGC TGT GAT CAG GAC GAG AAT GGG AAC CGA ACT TCA GTG GAT   336
CTG CGG ATA CGA AGG ACC CAG CAC TCG GTG CTG TCA CGG AAG TTT GTG   384
GAC GTC ATG ACA GAA TAC AAT GAA GCG CAG ATC CTG TTC CGG GAG CGA   432
AGC AAA GGC CGC ATC CAG CGC CAG CTG GAG ATC ACT GGG AGG ACC ACC   480
ACT GAC GAC GAG CTG GAA GAG ATG CTG GAG AGC GGG AAG CCG TCC ATC   528
TTC ATC TCG GAT ATT ATA TCA GAT TCA CAA ATC ACT AGG CAA GCT CTC   576
AAT GAG ATC GAG TCC CGC CAC AAA GAC ATC ATG AAG CTG GAG ACC AGC   624
ATC CGA GAG CTG CAC GAG ATG TTC ATG GAT ATG GCC ATG TTT GTC GAG   672
ACT CAG GGT GAA ATG GTC AAC AAC ATC GAG AGA AAT GTG GTG AAC TCT   720
GTA GAT TAC GTG GAA CAT GCC AAG GAA GAG ACG AAG AAA GCC ATC AAA   768
TAC CAG AGC AAG GCC AGG CGG AAA AAG TGG ATA ATT GCT GCT GTG GCG   816
GTG GCT GTC ATT GCC GTC CTG GCT CTA ATC ATT GGC TTG TCG GTT GGC   864
AAA TGA                                                            870
```

( 2 ) INFORMATION FOR SEQ ID NO:13:

( i ) SEQUENCE CHARACTERISTICS:
        ( A ) LENGTH: 867
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:13:

```
ATG CGG GAC CGG CTG CCC GAC CTC ACG GCG TGT AGG ACA AAC GAC GAT    48
GGA GAC ACT GCT GTC GTC ATT GTG GAG AAG GAT CAT TTC ATG GAC GGT    96
TTC TTC CAT CAG GTA GAG GAG ATT CGA AGC AGC ATA GCC AGG ATT GCT   144
CAG CAT GTA GAA GAC GTG AAG AAG AAC CAC AGC ATC ATC CTG TCT GCT   192
CCA AAC CCA GAA GGA AAA ATA AAA GAA GAG CTG GAG GAC CTG GAC AAA   240
GAG ATC AAG AAA ACT GCT AAC AGG ATC CGG GGC AAG CTG AAG TCT ATT   288
GAG CAG AGC TGT GAT CAG GAC GAG AAT GGG AAC CGA ACT TCA GTG GAT   336
CTG CGG ATA CGA AGG ACC CAG CAC TCG GTG CTG TCA CGG AAG TTT GTG   384
GAC GTC ATG ACA GAA TAC AAT GAA GCG CAG ATC CTG TTC CGG GAG CGA   432
AGC AAA GGC CGC ATC CAG CGC CAG CTG GAG ATC ACT GGG AGG ACC ACC   480
ACT GAC GAC GAG CTG GAA GAG ATG CTG GAG AGC GGG AAG CCG TCC ATC   528
TTC ATC TCG GAT ATT ATA TCA GAT TCA CAA ATC ACT AGG CAA GCT CTC   576
AAT GAG ATC GAG TCC CGC CAC AAA GAC ATC ATG AAG CTG GAG ACC AGC   624
ATC CGA GAG CTG CAC GAG ATG TTC ATG GAT ATG GCC ATG TTT GTC GAG   672
ACT CAG GGT GAA ATG GTC AAC AAC ATC GAG AGA AAT GTG GTG AAC TCT   720
```

-continued

```
GTA GAT TAC GTG GAA CAT GCC AAG GAA GAG ACG AAG AAA GCC ATC AAA    768
TAC CAG AGC AAG GCC AGG CGG AAG GTG ATG TTC GTC CTC ATT TGT GTA    816
GTC ACT TTG CTT GTG ATC CTT GGA ATT ATT CTC GCA ACA GCA TTG TCA    864
TAG                                                                 867
```

( 2 ) INFORMATION FOR SEQ ID NO:14:

( i ) SEQUENCE CHARACTERISTICS:
        ( A ) LENGTH: 840
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:14:

```
ATG CGG GAC CGG CTG CCC GAC CTC ACG GCG TGT AGG ACA AAC GAC GAT     48
GGA GAC ACT GCT GTC GTC ATT GTG GAG AAG GAT CAT TTC ATG GAC GGT     96
TTC TTC CAT CAG GTA GAG GAG ATT CGA AGC AGC ATA GCC AGG ATT GCT    144
CAG CAT GTA GAA GAC GTG AAG AAG AAC CAC AGC ATC ATC CTG TCT GCT    192
CCA AAC CCA GAA GGA AAA ATA AAA GAA GAG CTG GAG GAC CTG GAC AAA    240
GAG ATC AAG AAA ACT GCT AAC AGG ATC CGG GGC AAG CTG AAG TCT ATT    288
GAG CAG AGC TGT GAT CAG GAC GAG AAT GGG AAC CGA ACT TCA GTG GAT    336
CTG CGG ATA CGA AGG ACC CAG CAC TCG GTG CTG TCA CGG AAG TTT GTG    384
GAC GTC ATG ACA GAA TAC AAT GAA GCG CAG ATC CTG TTC CGG GAG CGA    432
AGC AAA GGC CGC ATC CAG CGC CAG CTG GAG ATC ACT GGG AGG ACC ACC    480
ACT GAC GAC GAG CTG GAA GAG ATG CTG GAG AGC GGG AAG CCG TCC ATC    528
TTC ATC TCG GAT ATT ATA TCA GAT TCA CAA ATC ACT AGG CAA GCT CTC    576
AAT GAG ATC GAG TCC CGC CAC AAA GAC ATC ATG AAG CTG GAG ACC AGC    624
ATC CGA GAG CTG CAC GAG ATG TTC ATG GAT ATG GCC ATG TTT GTC GAG    672
ACT CAG GGT GAA ATG GTC AAC AAC ATC GAG AGA AAT GTG GTG AAC TCT    720
GTA GAT TAC GTG GAA CAT GCC AAG GAA GAG ACG AAG AAA GCC ATC AAA    768
TAC CAG AGC AAG GCC AGG CGG CAA CAG CAT TGT CAT AGC AAC CGT ACC    816
CCA AGA GCT CTT TGT CCT CGG TGA                                    840
```

( 2 ) INFORMATION FOR SEQ ID NO:15:

( i ) SEQUENCE CHARACTERISTICS:
        ( A ) LENGTH: 2940
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
GGGCGGGCGG GCTGTGCCGT GGCAGCGCCT GCCCGAGGGA GGGCGGCGGC GCGGGCCAG      60
GACCCCGGCA GCAAGAGGCG GCGATCGGGC CACCGGAGAG TGTGCGGCGG GGCAGCTGAG    120
CGGCGGGTGC CCCGCCCTGC TGGCCGGTGG GG                                  152
ATG CGG GAC CGG CTG CCC GAC CTC ACG GCG TGT AGG ACA AAC GAC GAT     200
GGA GAC ACT GCT GTC GTC ATT GTG GAG AAG GAT CAT TTC ATG GAC GGT     248
```

```
TTC TTC CAT CAG GTA GAG GAG ATT CGA AGC AGC ATA GCC AGG ATT GCT      296
CAG CAT GTA GAA GAC GTG AAG AAG AAC CAC AGC ATC ATC CTG TCT GCT      344
CCA AAC CCA GAA GGA AAA ATA AAA GAA GAG CTG GAG GAC CTG GAC AAA      392
GAG ATC AAG AAA ACT GCT AAC AGG ATC CGG GGC AAG CTG AAG TCT ATT      440
GAG CAG AGC TGT GAT CAG GAC GAG AAT GGG AAC CGA ACT TCA GTG GAT      488
CTG CGG ATA CGA AGG ACC CAG CAC TCG GTG CTG TCA CGG AAG TTT GTG      536
GAC GTC ATG ACA GAA TAC AAT GAA GCG CAG ATC CTG TTC CGG GAG CGA      584
AGC AAA GGC CGC ATC CAG CGC CAG CTG GAG ATC ACT GGG AGG ACC ACC      632
ACT GAC GAC GAG CTG GAA GAG ATG CTG GAG AGC GGG AAG CCG TCC ATC      680
TTC ATC TCG GAT ATT ATA TCA GAT TCA CAA ATC ACT AGG CAA GCT CTC      728
AAT GAG ATC GAG TCC CGC CAC AAA GAC ATC ATG AAG CTG GAG ACC AGC      776
ATC CGA GAG CTG CAC GAG ATG TTC ATG GAT ATG GCC ATG TTT GTC GAG      824
ACT CAG GGT GAA ATG GTC AAC AAC ATC GAG AGA AAT GTG GTG AAC TCT      872
GTA GAT TAC GTG GAA CAT GCC AAG GAA GAG ACG AAG AAA GCC ATC AAA      920
TAC CAG AGC AAG GCC AGG CGG AAA AAG TGG ATA ATT GCT GCT GTG GCG      968
GTG GCT GTC ATT GCC GTC CTG GCT CTA ATC ATT GGC TTG TCG GTT GGC     1016
AAA                                                                  1019
TGATTGCGTA GATGGCGCTG GGTGCTTGCC TCTCCCTCAG GGTGGCAAAG GTGATGTTCG   1079
TCCTCATTTG TGTAGTCACT TTGCTTGTGA TCCTTGGAAT TATTCTCGCA ACAGCATTGT   1139
CATAGCAACC GTACCCCAAG AGCTCTTTGT CCTCGGTGAC TCCGACCATA CCTGCAGCTT   1199
AGTCAGCATC CTGTCCTTCC ACGAGTGAAC CTCAGACTCC AGGGCTAGCG CCGAGCACTG   1259
AGGTTTTTAT TGGTGATGAA GAAGAAAGCA CCGCAGAGGT TTCGTACCAT GAAACACCGC   1319
GAGCCCAGTG GATGCGACAT GCCAGCCCAG AGAGCCTGGG TCTCTCTCAA GGACACCACA   1379
GAGATTTCAC AACAGTGGCC TTGCCTTGGT AGCTTTGAAA TAGGAATGAT TGAAAAAGCC   1439
TAATTTTTAA AGACAATGTC AGTGTTAAAA ATGTATGTTG TGTGTAATTA GGGTGTGCTC   1499
TGCGCTCAGC TGGCAGTGCT GACGAAGAGA CTTCGAGCCA GGCCTGATCT CTGTTCATGT   1559
CTTGTTTGCA GAATCATCAC AGAACTGTTT TGTAAGGCAT CTGTAAGTTA AGTTCCTTAA   1619
TCTATTAACA TCTAAACTCC CTTTCTAAGC TAGACACTGC CTTGCGAAGG ACAATGGGCC   1679
AGCCCCGGGC AAGCATGAAC ACTGCCTTAC AGCCCCTCAG GGCCCTTCTA TAGTGCCTTC   1739
TGGTGACCCT GACTAGGAAG TGTGAGGGTC TGAAGAGCCT GAACGTTAG CTCACGGAGG    1799
GGACAAGCAG TCACATGCCG CACTCATGTT ACTCTCCCTT GTTCATGTGA GCTGATGAAG   1859
TCTCAAGGCA AGGCGACAGT GACGATGGAC CAAACTCGGT GCTCACTAAA CTCAAGAGAA   1919
TGGCCCCGAG TACATAGCCA CTCCTGGATG GCACCTGAAG GACCAGGTCC TCAGCCCAAC   1979
ACCCACGAGT GCCCAGAGTT CCTAAGAAAC CATGAAGTGT GGGATAAAGC TGTGCACTGG   2039
TTTACACTTG TGAATAGATG GCCCAGCGAC CAAGTATGTG AAGGATACCA TGACTAGTGA   2099
ACTCTGCCAA CTGCTGACTG TGATGAGTGC TCACTCTACC CCAGCCTCAC TTGGTGGGAT   2159
ATGACGTAGC CATGCCGGGT CAGAACACCA AGTGTGAGCA AGTGCTACTG AACTATCTAA   2219
AAACCATGAT CCTTTCAGTG GTAAGTGTGC CACACTGTCA CCTCCTCACA CCTTCTGGTC   2279
TGACACCCCA TGTGCCGAGA GCTACTGCAG CAGGCTGGGC TGTGGGTCCT GGTCTAGAGT   2339
TAGCCTGTAG TGCAGCCACT CCTGGCTGAT AGCTCACCCT TCCGCAACCG GGAGCTCACC   2399
```

-continued

```
CTTCCTGCCT GGAAGCTCAC ACTTCCTGTC TGGGAGCTCA CCCTTCTTGC CTGGGAGCTC 2459
ACACTTCCCG TCTGGGAGCT CACACTTCCT TCCTGGGAGC TCACACTTCC TGCCTGGGAG 2519
CTCACCCTTC CCGCCTGGGA GCTCACACTT CCTGCCTGGG AGCTCTGAAG ATGAACCTGG 2579
GCCTTTGCAG CTCACCCTCT CTGCATCAGT CAGTGCCATC GGATTTAGCT GCAGAGACCA 2639
TGCGTACCAC CCAGGCTCCC ACCACCCACA GCCAGGTGTC CCTCCAGTCC AGCCTGAGCC 2699
CTTGGCCTGC AGTGTGCTCG CAGAGCGCTC AGGAGACCTC TCGACCAGGC AGGCAGCTGA 2759
ATCTGGATTT CCAGTGAATC AGGGGTGTGT GGGTGACTGA GTCAGCACTC CAGATACATC 2819
TCTCTGCTGA CTTCATAGCC TATTTAAAAA TATATTTACA GATTCCCTTG TTACCTTTTC 2879
CAAGCATTTC TTCAAATATT TTGTGTTTAC ATTAAAAAGT TCTCAGAGAT GCAAAAAAAA 2939
A                                                                2940
```